United States Patent
Ward et al.

(10) Patent No.: US 9,845,168 B2
(45) Date of Patent: Dec. 19, 2017

(54) SOURCE FLUID INLET ASSEMBLY FOR AUTOMATED FILLING DEVICE

(71) Applicant: Baxter Corporation Englewood, Englewood, CO (US)

(72) Inventors: Brian William Ward, Littleton, CO (US); Cari Lyn Heffner, Castle Rock, CO (US); David Lee Holien, Parker, CO (US); Roy Sven Hovland, Denver, CO (US); James Robert Hutchison, Denver, CO (US); Richard Wayne LeVaughn, Canton, GA (US); Michael Dickson Olichney, Aurora, CO (US); Tammy Stultz, Westminster, CO (US); Jeffery Jonathan Rau, Littleton, CO (US); Yuriy Konstantinovich Umanskiy, Centennial, CO (US)

(73) Assignee: Baxter Corporation Englewood, Englewood, CO (US)

(*) Notice: Subject to any disclaimer, the term of this patent is extended or adjusted under 35 U.S.C. 154(b) by 169 days.

(21) Appl. No.: 14/984,022

(22) Filed: Dec. 30, 2015

(65) Prior Publication Data
US 2017/0190448 A1 Jul. 6, 2017

(51) Int. Cl.
| | | |
|---|---|---|
| G06F 7/00 | (2006.01) | |
| B65B 3/00 | (2006.01) | |
| A61J 1/20 | (2006.01) | |
| B65B 57/00 | (2006.01) | |

(52) U.S. Cl.
CPC ............ *B65B 3/003* (2013.01); *A61J 1/2048* (2015.05); *B65B 57/00* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,150,673 A * | 4/1979 | Watt | .......................... | A61J 1/10 |
| | | | | 128/DIG. 24 |
| 5,911,252 A * | 6/1999 | Cassel | ..................... | B65B 3/003 |
| | | | | 141/234 |
| 7,703,483 B2 * | 4/2010 | Hartman | ................. | B65B 3/003 |
| | | | | 141/27 |
| 8,807,177 B2 * | 8/2014 | Strangis | ................ | B63C 9/0005 |
| | | | | 141/104 |
| 2013/0000780 A1 * | 1/2013 | Garfield | ................ | A61J 1/2096 |
| | | | | 141/144 |
| 2014/0157731 A1 * | 6/2014 | Perazzo | .................. | B65B 57/02 |
| | | | | 53/473 |

(Continued)

*Primary Examiner* — Kyle Logan
(74) *Attorney, Agent, or Firm* — K&L Gates LLP

(57) ABSTRACT

A source fluid inlet for an automated filling device. The source fluid inlet may comprise features that limit engagement and/or disengagement of a source fluid tubing set from a port in the source fluid inlet except when the port is disposed in a predetermined load position. In turn, engagement and/or disengagement of the source fluid tubing may be selectively allowed to assist in reduction of interconnection errors of one or more source fluid sources. The source fluid inlet may selectively position a source fluid tubing set in a fill position to facilitate fluid communication with a receptacle to be filled (e.g., a syringe). The source fluid inlet further comprises one or more mechanisms for engagement and/or retention of a cap disposed on a syringe.

19 Claims, 32 Drawing Sheets

(56) References Cited

U.S. PATENT DOCUMENTS

2015/0000784 A1* 1/2015 Jamaledine ........... A61J 1/2096
                                                                             141/2
2015/0305982 A1* 10/2015 Bochenko ............. A61J 1/2096
                                                                            604/404

* cited by examiner

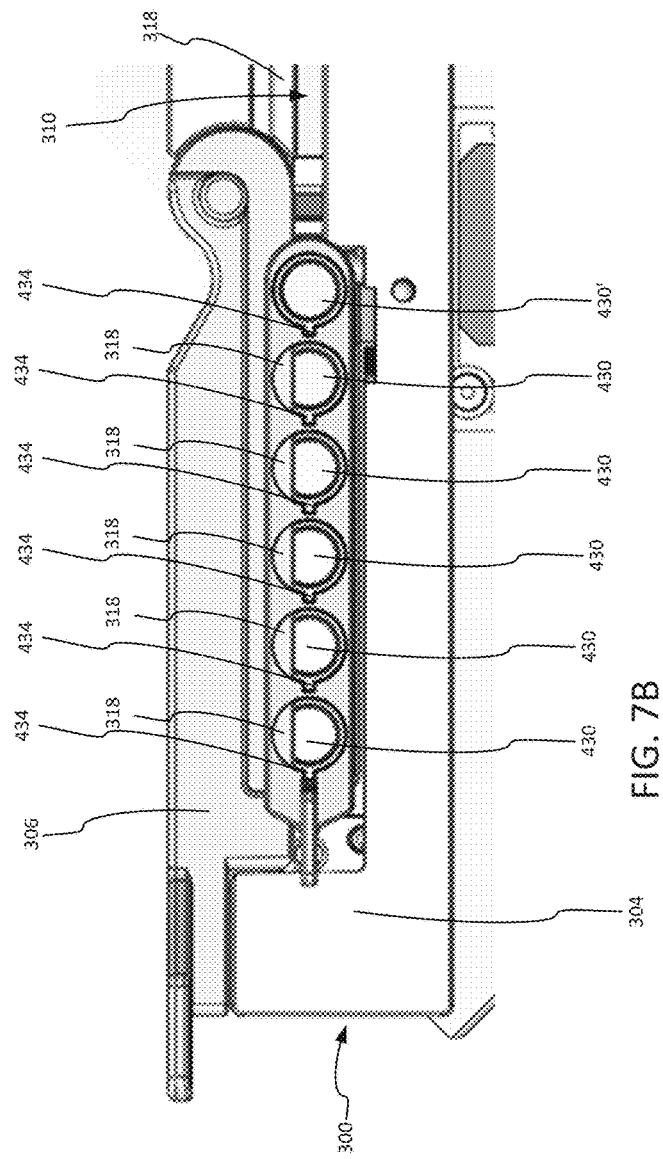

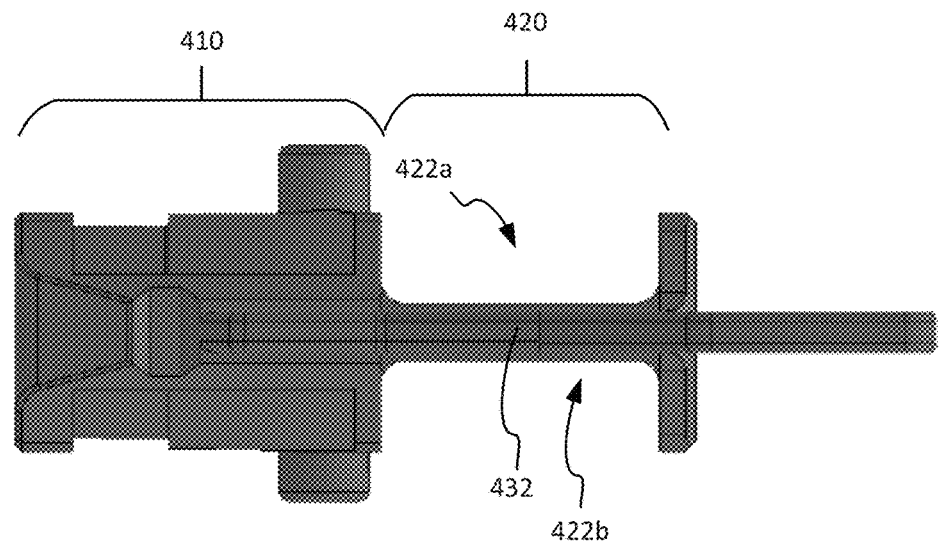
FIG. 24
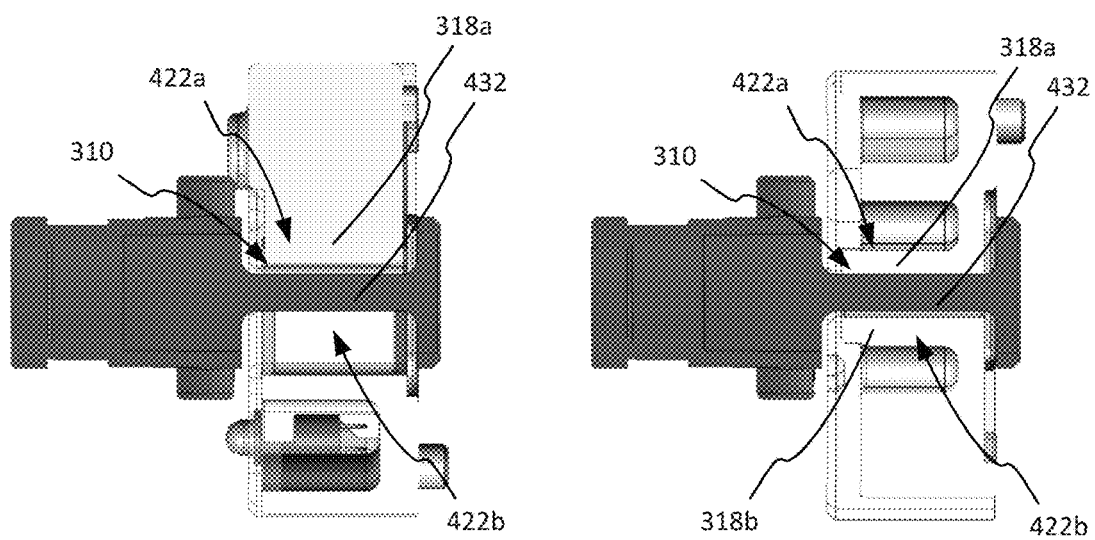
FIG. 25A
FIG. 25B

SOURCE FLUID INLET ASSEMBLY FOR AUTOMATED FILLING DEVICE

RELATED APPLICATIONS

This application relates to and incorporates by reference the co-owned application having Provisional Ser. No. 62/272,786 by Stultz et al. filed on Dec. 30, 2015 entitled SYRINGE POSITIONING APPARATUS AND METHOD. This application relates to and incorporates by reference the co-owned application having Provisional Ser. No. 62/272,789 by Umanskiy et al. filed on Dec. 30, 2015 entitled MEASUREMENT OF SYRINGE GRADUATION MARKS USING A VISION SYSTEM. This application relates to and incorporates by reference the co-owned application having Provisional Ser. No. 62/272,794 by Umanskiy et al. filed on Dec. 30, 2015 entitled CAPACITIVE SINGLE PLATE BUBBLE DETECTOR. This application relates to and incorporates by reference the co-owned application having Provisional Ser. No. 62/272,798 by Hutchison et al. filed on Dec. 30, 2015 entitled SYRINGE GRIPPING APPARATUS AND METHOD. This application relates to and incorporates by reference the co-owned application by Stultz et al. filed on Dec. 30, 2015 entitled SYRINGE PLUNGER POSITION APPARATUS AND METHOD. This application relates to and incorporates by reference the co-owned application having Provisional Ser. No. 62/272,816 by Ward et al. filed on Dec. 30, 2015 entitled INLET TUBE SET FOR SOURCE INGREDIENT DELIVERY. This application relates to and incorporates by reference the co-owned application by Stultz et al. filed on Dec. 30, 2015 entitled TIP CAP FOR AUTOMATIC SYRINGE FILING APPARATUS.

BACKGROUND

Automated filling devices may be used to prepare medications or other treatments in anticipation of administration to a patient. Automated filling devices may be used to fill syringes, bags, or other receptacles with fluid for administration to a patient. Such filling devices often include fluid interconnections to one or more fluid sources for use by the automated filling device. Such fluid sources may be vials, bags, or other appropriate receptacles that may be connected to a tubing set for transfer of the source fluid from a source fluid receptacle.

In turn, while automated filling devices may provide advantages (e.g., high accuracy and precision, rapid filling of receptacles, etc.) in relation to filling operations, oftentimes establishing the fluid interconnections with the fluid sources may require manual intervention by a user. This may introduce the potential for errors to occur (e.g., with incorrect fluid sources being connected or fluid sources being connected to an incorrect port of the automated filing device or the like). Furthermore, use of complex interfaces with fluid sources may result in relatively long fluid paths that create difficulties in connection with priming, purging, and other filling operations. This may result in waste or complexity in the filling operation to accommodate or account for the fluid in the fluid paths.

SUMMARY

In view of the foregoing, the present disclosure relates to a source fluid inlet assembly for an automated filling device. The inlet assembly may facilitate fluid communication between an automated filling device and one or more fluid sources. The inlet assembly may include features that assist a user manually connecting fluid sources to the inlet assembly. In turn, the potential for incorrectly connecting fluid sources to the automated filling device by a human user may be reduced.

For instance, the inlet assembly may include features that selectively prevent connection and/or disconnection of fluid sources except for when the inlet assembly is specifically configured to allow such connections and/or disconnections with respect to a given port. In this regard, the inlet assembly may include at least one port for accepting a connection to a fluid source. The inlet may also include structures that selectively allow connection and/or disconnection of a connector at a given port. The inlet assembly may be operative to dispose a port in a load position to facilitate connection and/or disconnection in relation to the port. However, when the port is away from the load position, the inlet assembly may block connection and/or disconnection of a connector in relation to the port. Accordingly, the ability to connect and/or disconnect a fluid source may be selectively controlled to reduce the potential for mistakes when connecting and/or disconnecting a fluid source with respect to the inlet assembly.

Additionally, the inlet assembly may provide a relatively simple interface for establishing fluid connection between a fluid source and a receptacle to be filled. Furthermore, the inlet assembly may provide for direct fluid communication between a tubing set connected to the source fluid and a receptacle to be filled. The inlet assembly may provide a relatively simple interface that reduces or minimizes a length of a fluid path. In turn, the inlet assembly may facilitate robust operation with a relatively low complexity interface for establishing fluid communication between a source fluid receptacle and a receptacle to be filled.

In addition, the inlet assembly described herein may be operative to dispose a port (e.g., that is engaged with a fluid source connector) in a position relative to a predetermined axis of an automated filling device. The automated filling device may facilitate movement of a syringe that is aligned with the predetermined axis along the predetermined axis. Accordingly, movement of the syringe along the predetermined axis may facilitate establishing fluid communication between the port and the syringe for filling of the syringe from the fluid source connector engaged with the port.

Further still, the inlet assembly described herein may facilitate grasping and/or retention of a cap from a syringe. This may allow a syringe having a cap to be decapped (e.g., prior to filling or for other operations such as syringe purging). The inlet assembly may be operative to retain the cap during filling. In turn, the syringe may be recapped after filling. Accordingly, a decapping mechanism may be provided with the inlet assembly described herein. The decapping mechanism may be alignable with the predetermined axis. In turn, movement of a syringe along the predetermined axis may facilitate engagement of a cap of a syringe with the decapping mechanism.

In an embodiment, movement of an inlet block linearly in a first dimension may facilitate movement of the inlet block between the one or more various positions of the inlet block (e.g., the load position, the fill position, the decapping position, etc.). A relatively simple drive arrangement may be provided to facilitate linear movement of the inlet block in the first dimension between the different positions. Furthermore, as the inlet block may be disposed in a plurality of positions such that various different components of the inlet block are disposed relative to a predetermined axis, simple movement of a syringe along the predetermined axis may be provided to facilitate establishing fluid communication, decapping, or other operations relative to a syringe. As such, the motion of the inlet block may be simple and robust and allow for relatively simple interfaces with the inlet block to accomplish one or more functions.

Accordingly, a first aspect includes a source fluid inlet for an automated filling device. The inlet includes an inlet block and a track. The inlet block includes a port configured to accept a source fluid tube set. The inlet block is engaged with the track. The track is defined by at least one rail. In turn, the inlet block and the track are disposed for relative movement between the inlet block and the track for positioning of the inlet block in a plurality of positions in a first dimension relative to the track. The positions at least include a load position and a fill position. In the load position, the port is aligned with a recess in the at least one rail to facilitate engagement of a source fluid tubing set with the port. In the fill position, the port is disposed relative to a predetermined axis along which a syringe is moveable for selective engagement of a syringe with a source fluid tubing set engaged with the port to establish fluid communication between a syringe and a source fluid tubing set engaged with the port.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, when away from the load position, the at least one rail extends relative to the port to prevent removal or insertion of a source fluid tubing set from the port. In this regard, unless the port is disposed in the load position, the source fluid tubing set may not be engaged with or disengaged with the port. In turn, control of the position of the inlet block may allow for engagement and disengagement with the port to be selectively controlled (e.g., to assist in reduction of errors when manually engaging source fluid receptacles to the inlet).

In an embodiment, the inlet block may include a shuttle and a cartridge. The shuttle may be disposed adjacent to the track for movement relative to the track (e.g., in a first dimension along which a slot defined by the at least one rail extends). The cartridge may define the port. The cartridge may include a first portion selectively engageable with the shuttle for co-movement with the shuttle and a second portion extending relative to the track for engagement with the track. In turn, the cartridge may be removable (e.g., for cleaning) and/or replaceable.

To facilitate engagement of the cartridge with the shuttle and slot defined in the track, the track may include a moveable portion that is operative to displace at least a portion of the rail to facilitate engagement of the cartridge with the shuttle. In this regard, the slot may be accessible to dispose the second portion within the slot. The moveable portion may include an interlock to detect when the moveable portion is in an open position relative to the track to prevent unauthorized or inadvertent removal of the cartridge from the shuttle and/or slot in the track.

The second portion of the cartridge may include a channel in which the at least one rail is disposed when the inlet block is away from the load position. In turn, a neck of a source fluid tube set may be aligned with the channel when engaged with the port such that a shoulder of a source fluid tube set travels at least a first distance beyond the channel in the port when a source fluid tube set is engaged with the port.

The inlet may further include a reader disposed relative to the inlet block to read a machine readable indicia provided on a source fluid tube set disposed in the port. In turn, an identity of the source fluid tube set may be determined by the inlet. This may be used to ensure that an appropriate source fluid has been connected and/or prevent reuse of tubing sets.

In an embodiment the inlet block includes a shuttle and a slide that may collectively define a cap retention cavity that may be moved between an open and closed position for engagement and/or retention of a cap of a syringe. The shuttle may be disposed adjacent to the track for movement relative to the track. The shuttle may include a first portion of the cap retention cavity. The slide member may include a second portion of the cap retention cavity.

The first portion of the cap retention cavity and the second portion of the cap retention cavity may be disposed for relative movement between an open position and a closed position upon relative movement between the shuttle and the slide. For example, the slide member may be supportably engaged by the shuttle and biased into the closed position by a biasing member. In turn, the slide may further include a tab engageable with a stop to restrict continued movement beyond a predetermined point in the first dimension. However, the shuttle may be moveable beyond the predetermined point to apply a force against a biasing force of the biasing member move the first portion of the cap retention cavity and the second portion of the cap retention cavity into the open position. Accordingly, the inlet block may be positionable in the first dimension relative to the track in a decapping position in which the cap retention cavity is aligned with the predetermined axis. A syringe having a cap disposed thereon may be moveable along the predetermined axis to dispose the cap in the cap retention cavity when in the open position such that the cap is retained in the cap retention cavity upon movement of the first portion of the cap retention cavity and the second portion of the cap retention cavity to the closed position.

In an embodiment, the source fluid inlet may also include a cap gripping device that may also be utilized to engage and/or retain a cap. The cap gripping device may include a first jaw member and a second jaw member. The first jaw member and the second jaw member may be disposable in an open position and a closed position, wherein the cap gripping device is disposed in relation to a second predetermined axis offset and parallel to the predetermined axis.

The cap gripping device may be actuated by the inlet block when the inlet block is moved into an actuation position. For instance, the first jaw member may include a first cam follower and the second jaw member may include a second cam follower. The first cam follower and the second cam follower may be engaged by corresponding respective cam surfaces on the inlet block when the inlet block is in the actuation position in the first dimension to move the first and second cam followers in a common direction to dispose the first jaw member and the second jaw member in the closed position. The predetermined axis and the second predetermined axis may define a plane extending in two dimensions. In turn, a syringe positioning apparatus may be operative to move a syringe in the two dimensions. The first dimension along which the inlet block may be moved extends at an angle relative to the plane.

As such, the inlet block may comprise a cap retention cavity that may be used to engage and/or retain a cap on a syringe aligned on the predetermined axis and may include a cap gripping device that can engage and/or retain a cap on a syringe aligned on the second predetermined axis. As the axes may define a plane, a relatively simple syringe gripping apparatus may be used that may move in the two dimensions of the plane to move a syringe between the two axes and along either axis to facilitate decapping of a syringe. In turn, the cap retention cavity and/or cap gripping device may be used in connection with filling or purging operations (e.g., each performed at a respective corresponding one of the devices).

In an embodiment, the inlet may include a bubble sensor for monitoring the source fluid tubing set during filling. Specifically, the inlet may include a single plate capacitive sensor disposed along the track such that the single plate captive sensor is operative to monitor the source fluid tubing set engaged with the port when in the fill position. The single plate capacitive sensor is disposed on only a first side of the source fluid tubing set. The single plate capacitive sensor is disposed in the at least one rail that is disposed relative to a neck of the source fluid tube set engaged with the port. Accordingly, as the single plate capacitive sensor is dispose on only one side of the tubing, the tubing may not need to be placed specifically between a pair of sensors. As such, when the inlet block moves the port into the fill position, the tubing set engaged with the port may automatically be aligned with the sensor for monitoring of the tubing.

In an embodiment, the source fluid tubing set may include a connector configured for engagement with the port when in the load position. The connector may include a sheath having at least one finger disposed distal relative to a fill connection of the connector. In this regard, the one or more fingers may extend relative to the fill connection to at least partially guard the fill connection (e.g., to prevent contact of the fill connection with a surface prior to engagement with the port). In turn, the sheath may engage the port when the connector is advanced distally relative to the port to limit distal movement of the sheath such that a first portion of the connector comprising the fill connection is advanceable distally relative to the sheath upon engagement of the connector with the port to dispose the fill connection distal relative to the at least one finger to expose the fill connection when the connector is fully seated in the port. In addition, the first portion of the connector may include a shoulder that is advanceable distally relative to the rail when the port is in the load position, and wherein when the port is away from the load position, the shoulder engages the rail to prevent proximal movement of the connector relative to the port.

BRIEF DESCRIPTION OF THE DRAWINGS

FIG. 7B depicts an elevation view of an embodiment of a cartridge with a port disposed in a fill position and a plurality of ports away from the fill position.

FIG. 24 depicts an elevation view of an embodiment of a cartridge that may be utilized in connection with a source fluid inlet assembly.

FIGS. 25A and 25B depict cross sectional views of an embodiment of a track having a cartridge engaged therewith.

DETAILED DESCRIPTION

Figure 1:
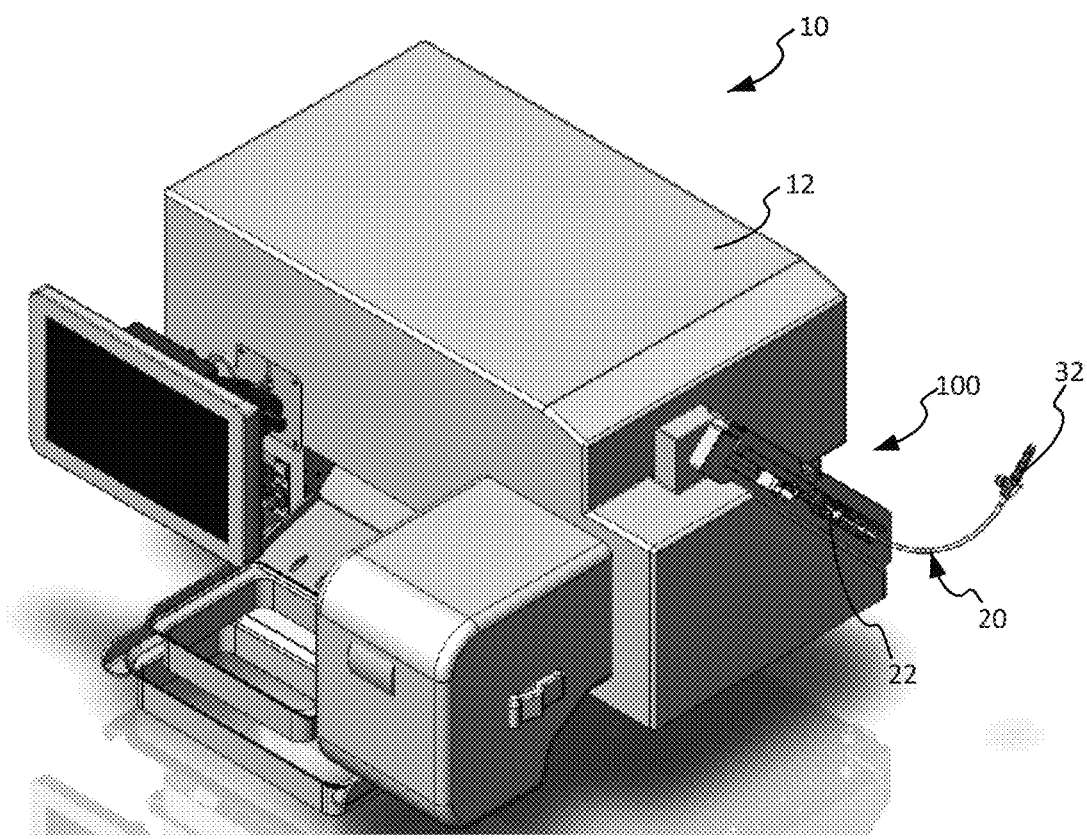
FIG. 1 depicts a perspective view of an embodiment of an automated fill device that includes a source fluid inlet assembly.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

With reference to FIG. 1, the present disclosure generally relates to a source fluid inlet assembly 100 that may be utilized in connection with an automated filling device 10. The automated filling device 10 may have a housing 12 within which the components of the automated filling device 10 are disposed. The automated filling device 10 may have components for aligning, moving, or otherwise manipulating a receptacle to be filled. For instance, the automated filling device 10 may be a syringe filler capable of manipulating a syringe 14 (not shown in FIG. 1) as will be described in greater detail below.

The automated filling device 10 may comprise a source fluid inlet assembly 100. At least a portion of the source fluid inlet assembly 100 may be disposed such that the source fluid inlet assembly 100 is accessible from an exterior of the housing 12. In this regard, a source fluid tubing set 20 may be selectively engaged with the source fluid inlet assembly 100 to establish fluid communication between a fluid source (not shown) and the automated filling device 10 as will be described in greater detail below. For instance, the source fluid tubing set 20 may have a connector 22 at a first end portion thereof and a source receptacle connection 32 at a second end thereof. An embodiment of the connector 22 is described in greater detail below. The source receptacle connection 32 may be a spike, luer fitting, needle, or any other appropriate connection for establishing fluid communication with a source fluid receptacle such as a bag, vial, or other source fluid receptacle.

Figure 2:
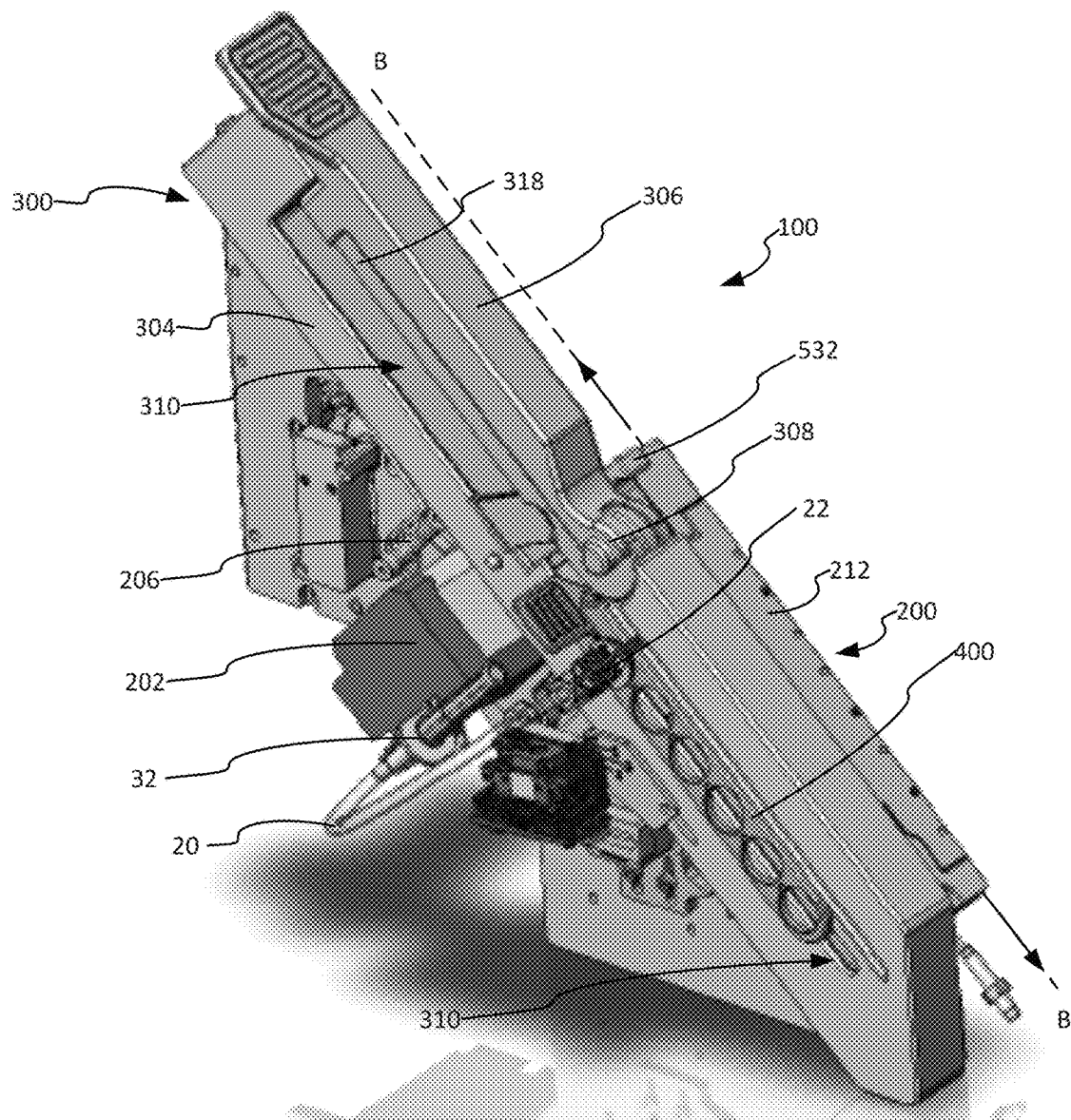
FIGS. 2 and 3 depict perspective views of an embodiment of a source fluid inlet assembly.
Figure 3:
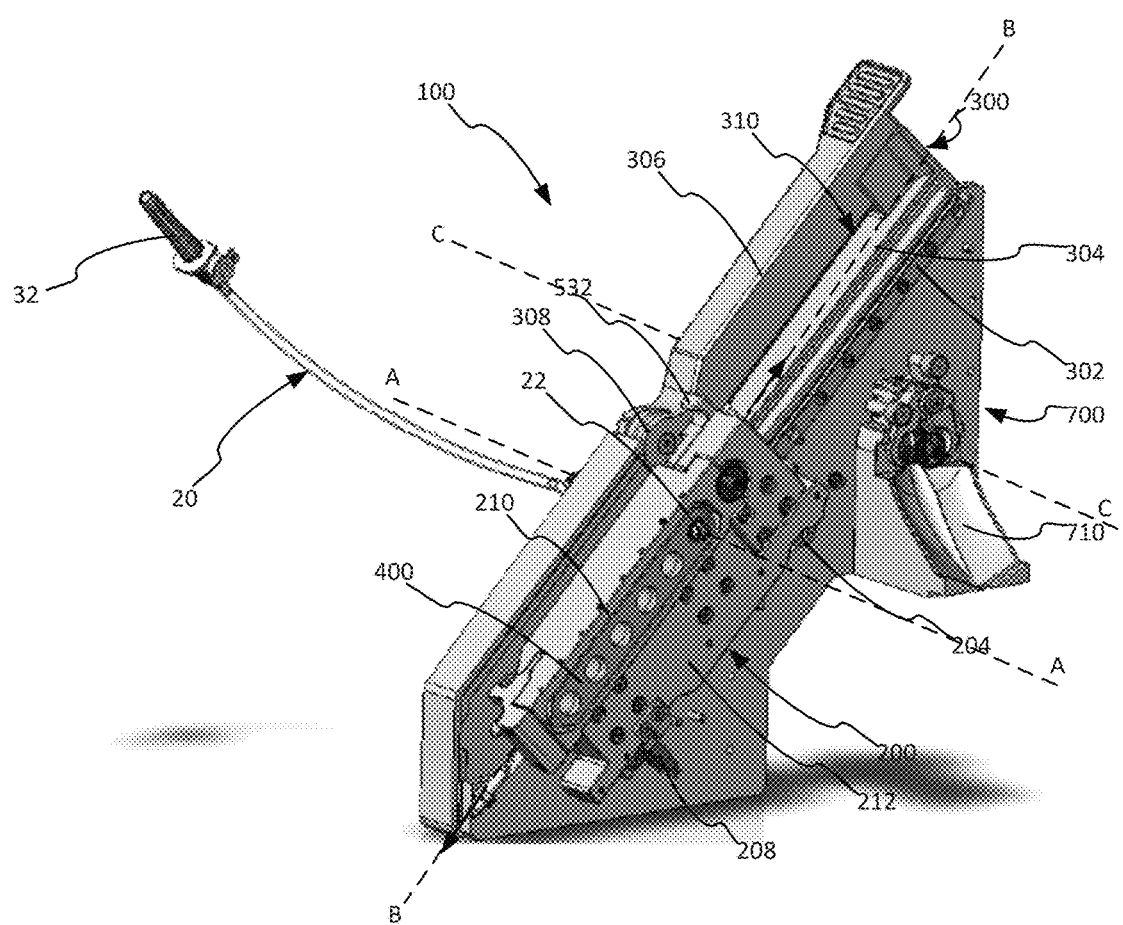

With further reference to FIGS. 2 and 3, the source fluid inlet assembly 100 is depicted in isolation (i.e., without the housing 12 of the automated filling machine 10) for clarity. FIG. 2 depicts a perspective view of the source fluid inlet assembly 100 as would be seen from an exterior of the automated filling device 10. FIG. 3 depicts a perspective view of the source fluid inlet assembly 100 as would be seen from an interior of the automated filling device 10.

Figure 4:
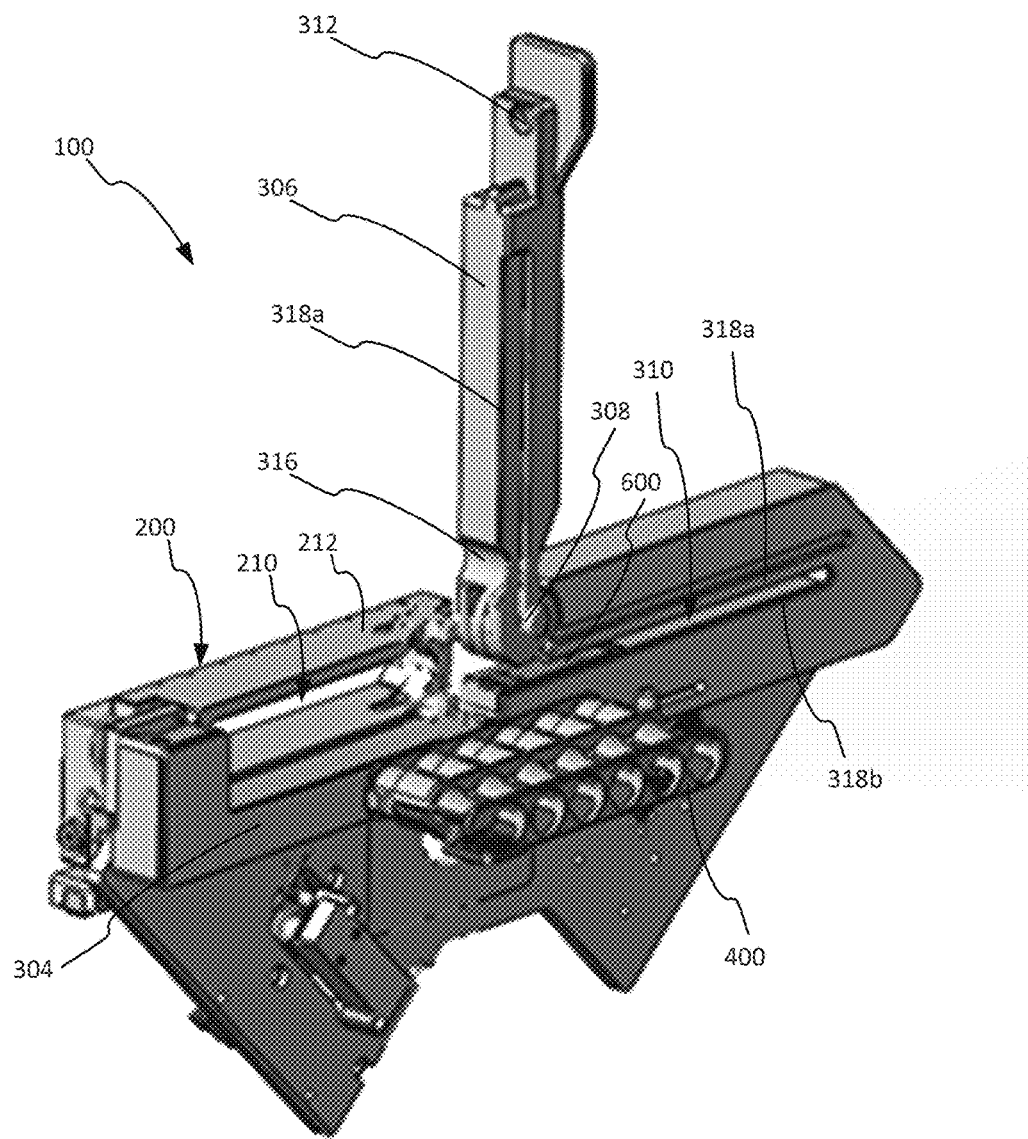
FIGS. 4 and 5 depict perspective views of an embodiment of a source fluid inlet assembly with a track member in an open position to facilitate engagement of a cartridge with a shuttle of an inlet block.

The source fluid inlet assembly 100 may include an inlet block 200 and a track 300. The inlet block 200 may be movable relative to and generally along the track 300 such that the inlet block 200 travels in a first dimension along axis B-B. The track 300 may include a slot 310 that extends in the first dimension parallel to axis B-B. In this regard, the inlet block 200 may be moved along the length of the slot 310 as described in greater detail below. The slot 310 may be defined by at least one rail 318 that extends along at least one side of the slot 310. As depicted in FIG. 4, the slot 310 may be defined by a first rail 318*a* and a second rail 318*b*. At least portions of the first rail 318*a* and the second rail 318*b* may be opposed to define opposite sides of the slot 310. At least one rail member 318 may extend along substantially the entire length of the slot 310. In an embodiment, opposing rails 318*a* and 318*b* may be positioned on either side of the slot 310 along at least a portion, and potentially the entire length, of the slot 310.

In this regard, and is best seen in FIGS. 2 and 3, a linear bearing 302 may be fixed to the track 300 relative to the slot 310 and may define a path along which the inlet block 200 may travel in the first dimension along axis B-B. A motor 202 may be supportably engaged by the track 300. The motor 202 may drive a pinion gear 204 as seen in FIG. 3. The pinion gear 204 may be positioned relative to the inlet block 200 such that the pinion gear 204 may mesh with a rack 214 (shown in FIG. 13) disposed on the inlet block 200. In this regard, activation of the motor 202 may result in rotation of the pinion gear 204 that meshes with the rack 214 on the in the inlet block 200 to move the inlet block 200 along the linear bearing 302 relative to the track 300. In this regard, the inlet block 200 may be moved linearly in a first dimension parallel to the extent of the slot 310 (e.g., along axis B-B).

Figure 10:
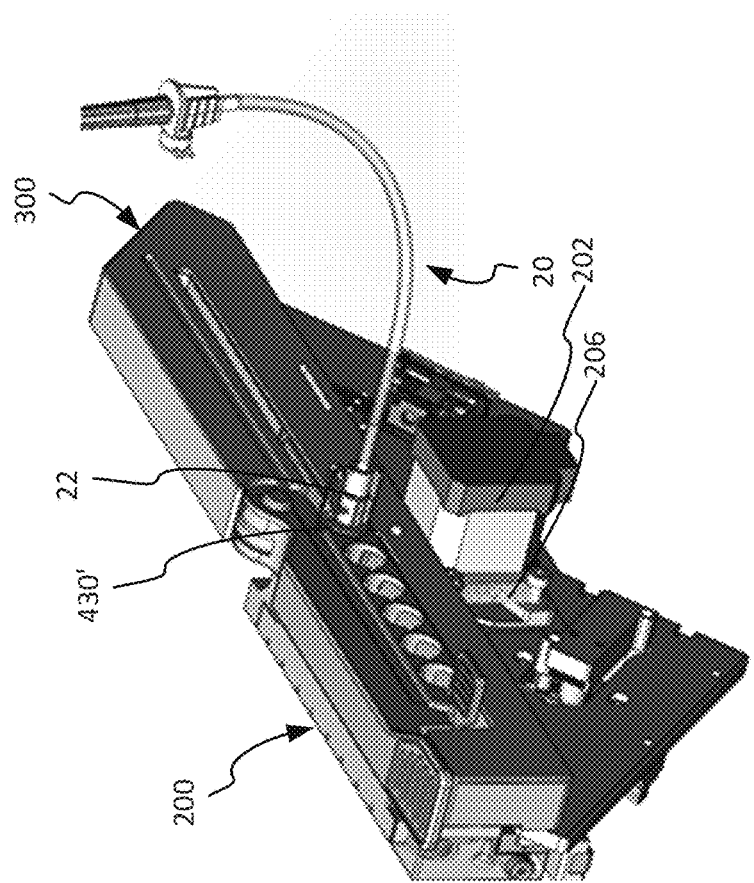
FIG. 10 depicts a perspective view of an embodiment of a connector of a source fluid tubing set engaged with a port.
Figure 9:
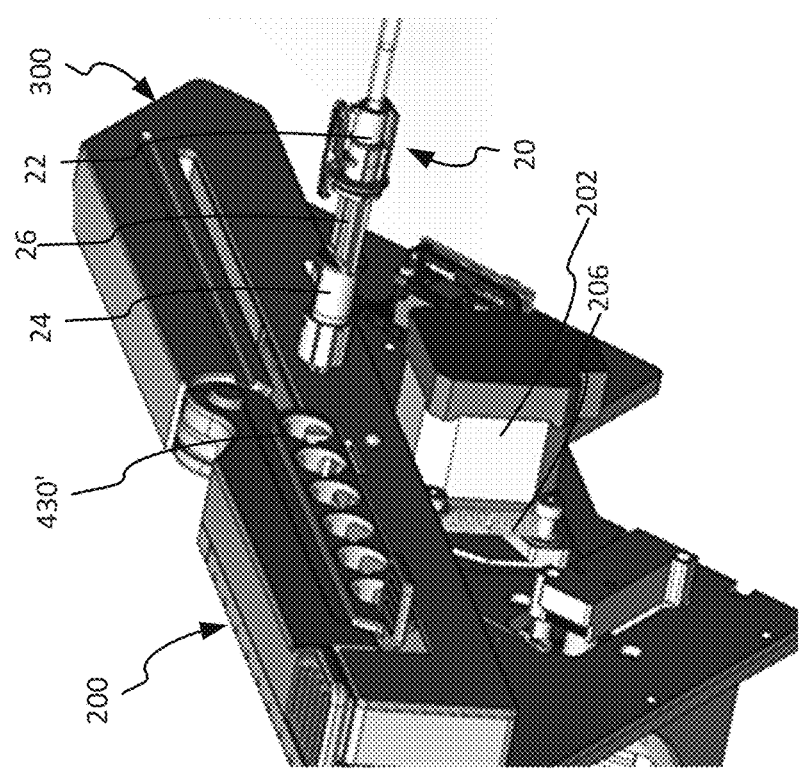
FIG. 9 depicts a perspective view of an embodiment of a connector of a source fluid tubing set disengaged from a port.

The motor 202 may be pivotally mounted to the track 300 to allow for the motor 202 to move rotationally about an axis perpendicular to the axis B-B along which the inlet block 200 may be moved. In turn, a biasing member 206 (e.g., a spring member) (FIG. 10) may be engaged with motor 202 to bias the motor 202 such that the pinion gear 204 is biased in meshed engagement with the rack on the inlet block 200.

As will be appreciated from the discussion below, the motor 202 may be selectively controlled to position the inlet block 200 in a plurality of positions along the axis B-B relative to the track 300. Accordingly, a homing sensor 208 may be provided. The homing sensor 208 may be operative to sense the inlet block 200 when disposed in a home position. This may allow for the establishment of the home position of the inlet block 200 such that precision motor control of the motor 202 (e.g., the use of a stepper motor or the like) may allow for precise positioning of the inlet block 200 relative to the track 300 in a plurality of predetermined positions along the axis B-B.

Figure 5:
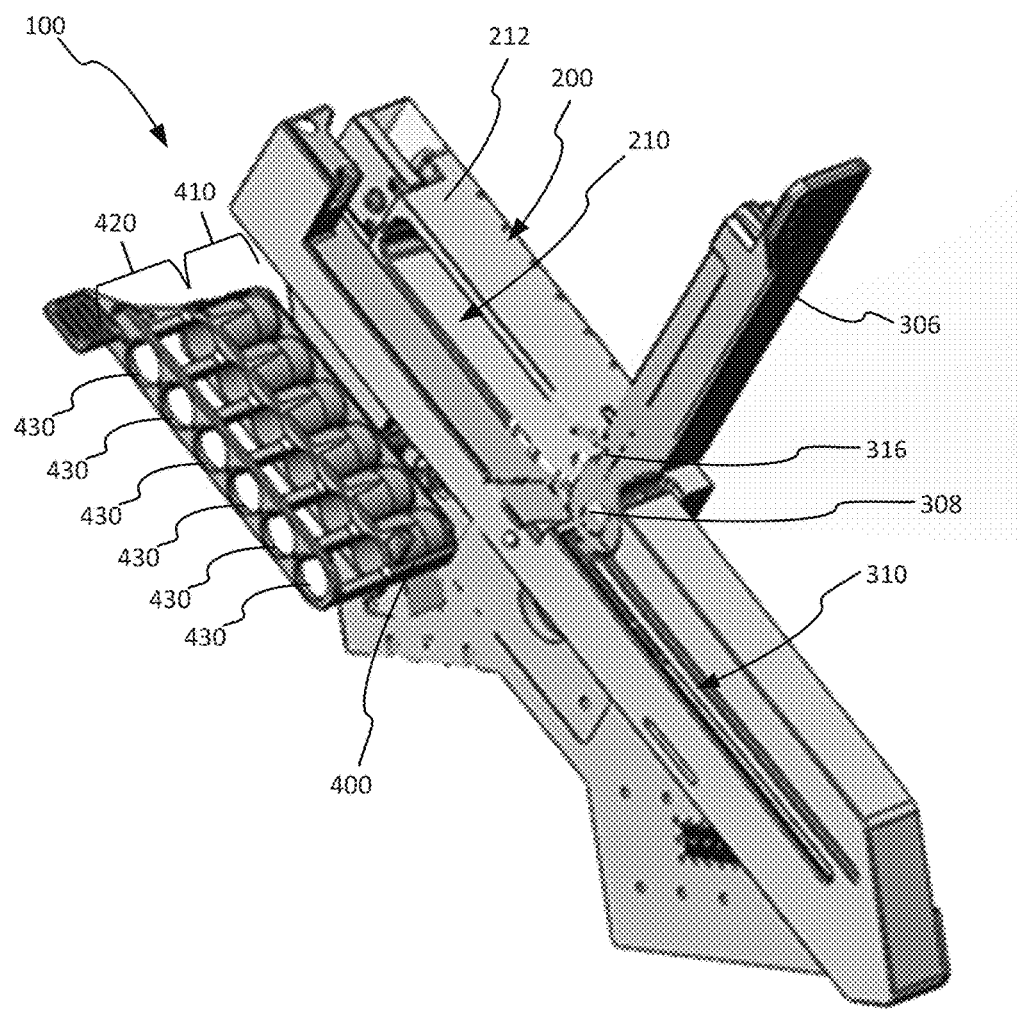

The track 300 may comprise a plurality of members that collectively define the slot 310. For instance, the track 300 may include a first track member 304 and a second track member 306. The second track member 306 may be engaged with the first track member 304 at a pivot 308. In turn, the first track member 304 and the second track member 306 may collectively define the slot 310 that extends in the first dimension parallel to axis B-B along which the inlet block 200 may be positioned. The slot 310 may at least partially be defined by the second track member 306 such that the second track member 306 may be pivotal relative to the pivot 308 and may be moveable away from the first track member 304 to provide an opening in the slot 310 for access to the interior of the slot 310. That is, the second track member 306 may be disposed in an open position (e.g., as shown in FIGS. 4 and 5) and a closed position (e.g., as shown in FIGS. 2 and 3). In this regard, the second track member 306 may comprise an access door that allows for selective access to the interior of the slot 310. Upon disposing the second track member 306 in a closed position, the perimeter of the slot 310 may be continuous. Accordingly, as will be described in greater detail below, the slot 310 may capture a portion of the inlet block 200 (e.g. a portion of a cartridge 400 described below) to allow for movement along the slot 310, but prevent removal of the portion of the inlet block 200 from the slot 310.

The inlet block 200 may include a cartridge 400 that defines a port 430 that may be engageable with a connector 22 of a source fluid tubing set 20. The cartridge 400 may be at least partially disposed relative to the track 300. For instance, the cartridge 400 may interface with a shuttle 212 to dispose the cartridge 400 relative to the track 300 when engaged with the shuttle 212. In turn, the track 300 (e.g., one or more rail members 318 of the track 300) may interface with the cartridge 400 when engaged with the shuttle 212. In turn, positioning the cartridge 400 relative to certain features of the track 300 may allow for selective engagement and/or disengagement of a connector 22 with the port 430 as described below. Furthermore, movement of the cartridge 400 relative to the track 300 may position the port 430 in a number of predefined positions (e.g., positions related to operations of the automated filling device 10). The following discussion begins with a discussion of cartridge 400 including the engagement and disengagement thereof with the inlet block 200. Subsequently, the engagement of a connector 22 with a port 430 of the cartridge 400 is discussed. Thereafter, the interaction of the cartridge 400 and/or connector 22 with the rail 300 is described in relation to selective engagement and disengagement of the connector 22 with respect to the port 430.

It may be advantageous to prevent and/or detect when the second track member 306 is in the closed or open position. For instance, the second track member 306 may be opened during loading of the cartridge 400. However, during other operations of the inlet assembly 10 (e.g., when the inlet block 200 is in another position other than the position for cartridge loading and unloading), the second track member 306 is preferably disposed in the closed position to reduce the potential for unintentional disengagement of the cartridge 400 from the shuttle 212. As such, the track 300 may include an interlock device that may operative to detect when the second track member 306 is disposed in the open and/or closed position. For example, the track 300 may include a sensor 314 that may detect the presence of a contact 312 in the second track member 306. Specifically, the contact 312 may be positioned relative to the sensor 314 when the second track member 306 is in the closed position. Accordingly, when the inlet assembly 100 detects the second track member 306 in the open position other than during a cartridge load operation 400, the inlet block assembly 100 may communicate a fault to the automated filling device 10 that may cease operation. In this regard, the second track member 306 may be allowed to be positioned in the open position only during a cartridge load or unload operation in which the shuttle 212 is in the cartridge load position shown in FIGS. 4 and 5. Other interlocks such as a physical interlock that prevents opening of the second track member 306 may also be provided. Further still, different sensor arrangements may be provided to monitor the second track member 306 to determine whether the second track member 306 is in an open or closed position.

Figure 7A:
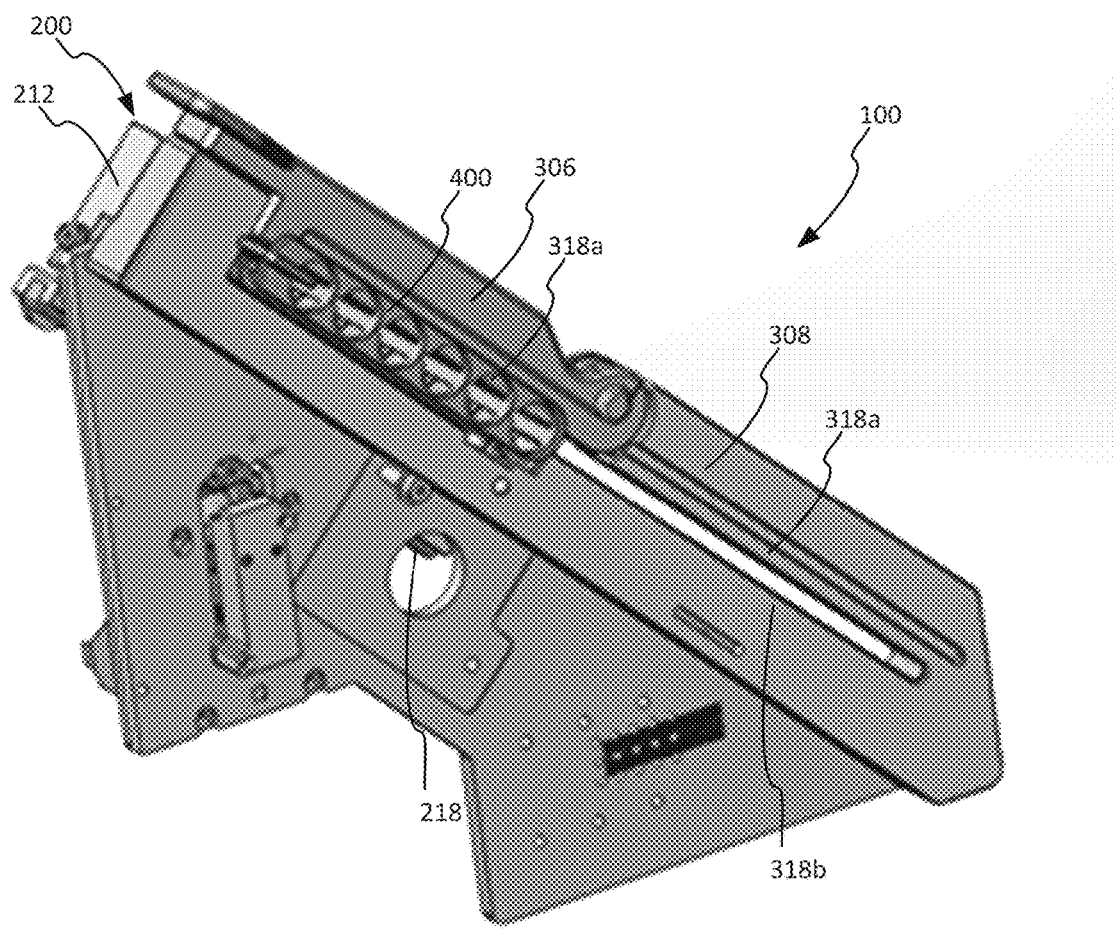
FIG. 7A depicts a perspective view of an embodiment of a source fluid inlet assembly with a cartridge engaged with a shuttle and track of the assembly.

As mentioned above, the inlet block 200 may comprise a shuttle 212 that may include an aperture 210 for receiving a cartridge 400. In this regard, the cartridge 400 may be engaged by the shuttle 212 to collectively comprise the inlet block 200. In turn, the cartridge 400 and shuttle 212 may collectively be referred to as the inlet block 200. In FIGS. 4 and 5, the cartridge 400 is shown in a disengaged position relative to the in the block 200. However, FIGS. 2, 3 and 7A depict the cartridge 400 engaged with the shuttle 212 (i.e., received in the aperture 210). When the cartridge 400 is engaged with the shuttle 212, the cartridge 400 may be moved with the shuttle 212. In this regard, as the shuttle 212 moves in the first dimension along axis B-B, the cartridge 400 may be engaged for comovement with the shuttle 212 parallel to the axis B-B. As the cartridge 400 may be selectively engaged and disengaged with the shuttle 212, the cartridge 400 may be selectively removable for cleaning and/or replacement of the cartridge 400. That is, the cartridge 400 may be periodically removed to be cleaned and/or may be replaceable (e.g., may be a disposable item that is periodically replaced).

Figure 23:
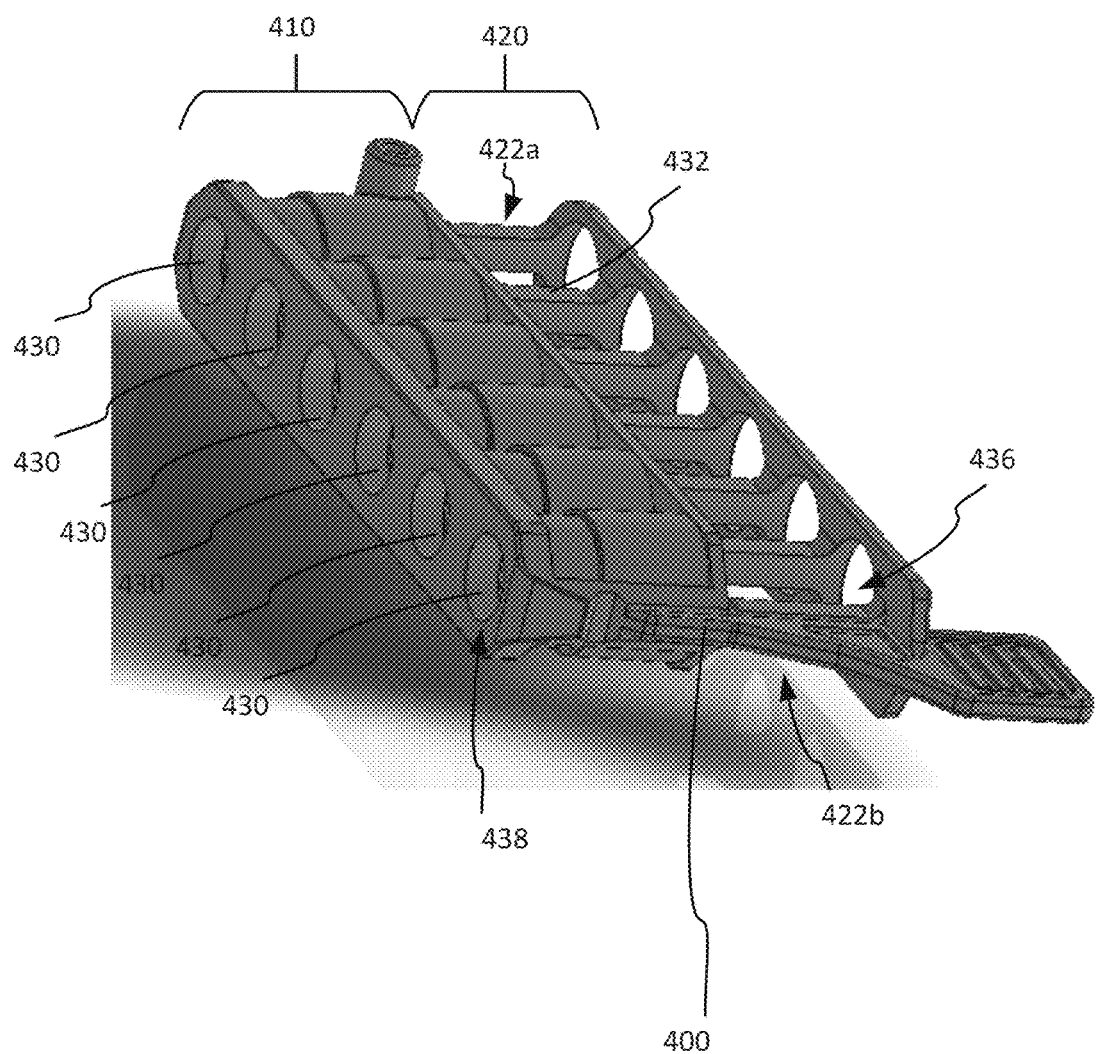
FIG. 23 depicts a perspective view of an embodiment of a cartridge that may be utilized in connection with a source fluid inlet assembly.

The cartridge 400 may comprise a first portion 410 and a second portion 420 as shown best in FIGS. 23 and 24. The first portion 410 is generally engageable with the aperture 210 of the shuttle 212 such that the cartridge 400 is moved with the shuttle 212 when engaged therewith. The cartridge 400 further includes a second portion 420 that may be engaged with the slot 310 as will be described in greater detail below.

The cartridge 400 may only be engageable or disengageable with the shuttle 212 and slot 310 when the shuttle 212 is in a cartridge load position shown in FIGS. 4 and 5 and the second track portion 306 is opened as shown in FIGS. 4 and 5. Specifically, as shown in FIG. 4, upon positioning the second rail member 306 in the open position, the aperture 210 may be exposed to accept the cartridge 400. That is, a first rail member 318a may extend along one side of the slot 310 and a second rail member 318b may extend along at least a portion of the second side of the slot 310. The first rail member 318a may be collectively defined by the first track member 304 and the second track member 306. In this regard, when the second track member 306 is in the open position, the first rail member 318a defined by the second track member 306 may be displaced from the slot 310 so that the cartridge 400 may be disposed in the aperture 210. As the second rail member 318b may not extend along the slot 310 adjacent to the aperture 210 when in the cartridge load position, the second rail member 318b may not interfere with engagement of the first portion 410 of the cartridge 400 with the aperture 210. Once the cartridge 400 is engaged with the aperture 210, the second rail member 306 may be moved to the closed position to dispose the first rail member 318a relative to the second portion 420 of the cartridge 400 as will be described in greater detail below.

The cartridge 400 may include at least one port 430 that may be engaged with a connector 22 of the source fluid tubing set 20. As may be appreciated, in the embodiment depicted, the cartridge 400 may include a plurality of ports 430. However, each of the ports 430 may have common characteristics as described herein in relation to a single port 430. In this regard, it is contemplated that an embodiment of the inlet assembly 100 may include a single port 430 without limitation. The port 430 may be configured to engage with a source fluid tubing set 20. For instance, the port 430 may be generally cylindrical to accept a correspondingly shaped cylindrical connector 22 of the source fluid tubing set 20.

Figure 27A:
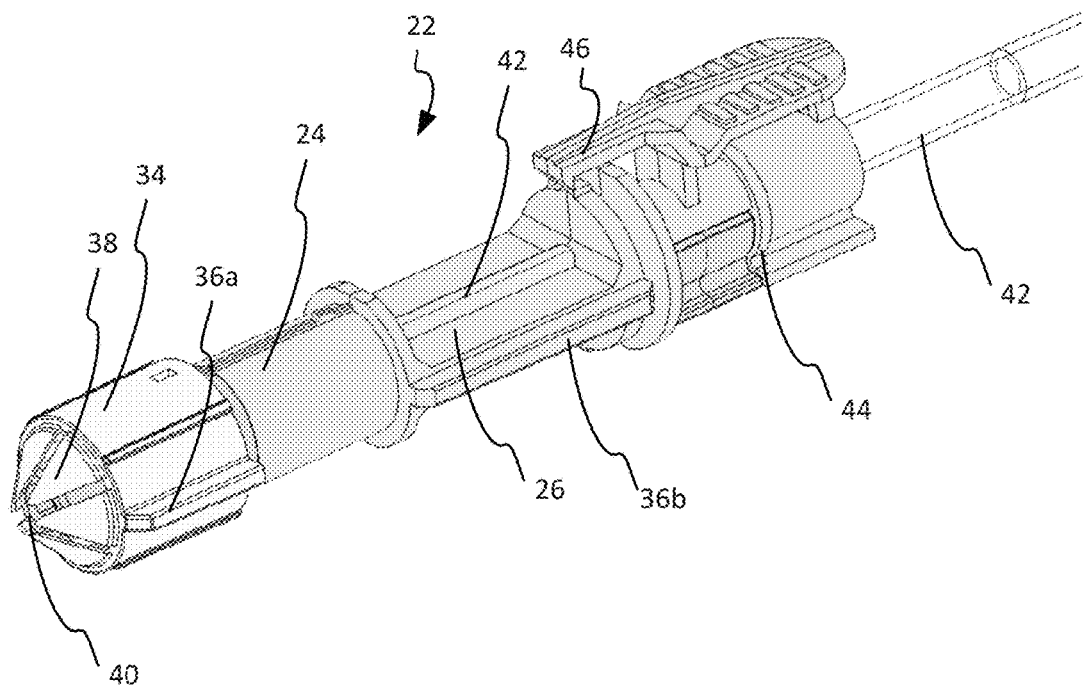
FIGS. 27A and 27B depict perspective views of an embodiment of a connector for a source fluid tubing set.
Figure 27B:
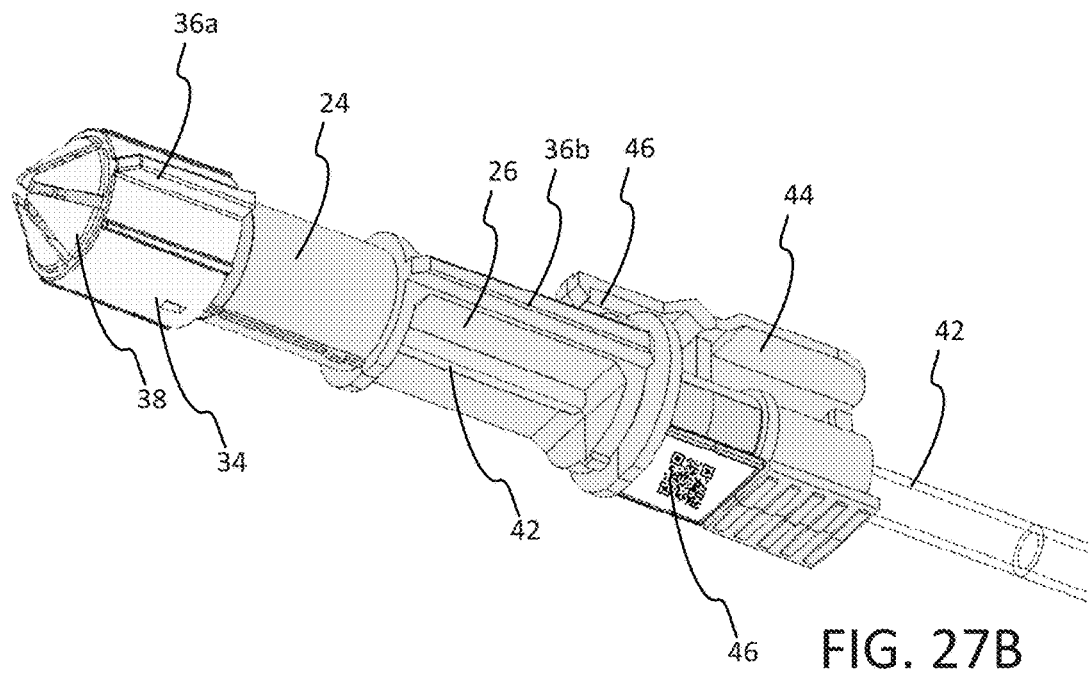

Specifically, the source fluid tube set 20 may include a connector 22 as depicted in FIGS. 27A and 27B. The port 430 may be generally shaped to receive the connector 22 of the source fluid tubing set 20. For example, the port 430 may be shaped correspondingly to the connector 22 for engagement therewith.

With additional reference to FIGS. 27A and 27B, the connector 22 may include a first connector portion 24, a neck 26, and a second connector portion 44. The first connector portion 24 may be disposed distally relative to the neck 26, and the second connector portion 44 may be proximal relative to the neck 26. The connector 22 may also include a sheath 34 that is initially disposed adjacent to the distal end of the first connector portion 24. The first connector portion 24 may comprise a fill connection 40 that may be engageable with a syringe to establish fluid communication between the syringe and the source fluid tubing set 20. The sheath 34 may include fingers 38 that extend distally from the sheath 34. The fingers 38 may at least partially cover the fill connection 40 when the sheath 34 is in the distal position as shown in FIGS. 27A and 27B. The sheath 34 may further include a flange 36a that extends from the sheath 34.

The first connector portion 24 may be substantially cylindrical such that the first connector portion 24 may have a circular cross section. In this regard, the first connector portion 24 may have a corresponding first cross sectional extent (e.g., a first diameter). The neck 26 may be substantially planar. In this regard, the cross sectional area of the neck 26 may be less than the cross sectional area of the first connector portion 24. Furthermore, the planar shape of the neck 26 may have a thickness that may be equal to or less than the thickness of the tubing 42 of the tubing set 20. As such, a portion of the tubing 42 may be exposed on a first and/or a second side of the neck 26 corresponding to a respective first and/or second planar side of the neck 26. Additionally, the neck 26 may comprise a flange 36b.

The second connector portion 44 may be disposed proximally to the first connector portion 24 and the neck 26. The second connector portion 44 may comprise a clip 46 that may be engageable with the cartridge 400 and/or shuttle 212 to assist in securing the connector 22 relative to a port 430 when advanced relative to the port 430. The second connector portion 44 may also comprise indicia 46. The indicia 46 may comprise a machine readable indicia that may be unique to and/or associable with the given tubing set 20.

With further reference to FIG. 23, the port 430 may extend though both the first portion 410 and the second portion 420 of the cartridge 400. The port 430 may have a distal opening 438 and proximal opening 436. In the first portion 410 adjacent to the distal opening 438, the port 430 may comprise a cylindrical passage adapted to engage the connector 22. For instance, the first portion 410 of the cartridge 400 may be correspondingly shaped to the first connector portion 24 (e.g., the port 430 may have an inner diameter corresponding to the first diameter of the first connector portion 24 such that the first connector portion 24 may be received by the first portion 410 of the cartridge 400). The port 430 may also extend through a second portion 420 to the proximal opening 436. In the second portion 420, a bridge 432 may extend along the port 430. In this regard, a first channel 422a may be defined in the second portion 420 that may extend relative to the port 430 on a first side of the cartridge 400. A second channel 422b may extend relative to the port 430 on a second side of the cartridge 400. That is, the only portion of the cartridge 400 that extends relative to the port 430 in the second portion 420 may be the bridge 432 such that the channel 422 is defined relative to at least a portion of the cross sectional area of the port 430 in the second portion 420. The bridge 432 may be configured to correspond to the neck 26 of the connector 22 as will be discussed in greater detail below.

Figure 28:
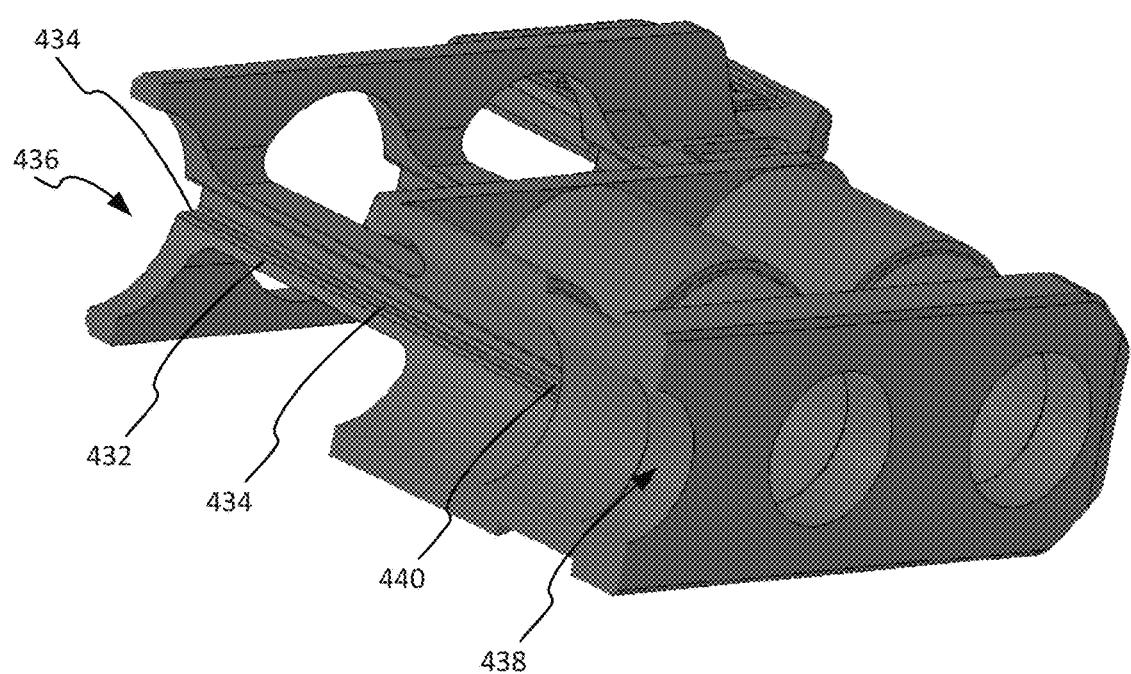
FIG. 28 depicts an embodiment of a cartridge shown in cross section along a port of the cartridge.

With further reference to FIG. 28, the port 430 may comprise a groove 434 that extends from the proximal opening 436 of the port 430 distally. As may be appreciated, the groove 434 may terminate prior to the distal opening 438 of the port 430. In this regard, the flange 36a on the sheath 34 may be correspondingly sized to engage the groove 434. In turn, the connector 22 may be aligned (e.g., rotationally aligned) with the port 430 when the flange 36a is aligned with the groove 434. In turn, the connector 22 may be advanced distally toward the distal opening 438 of the port 430. In doing so, the flange 36a may be advanced in the groove 434. In turn, the flange 36b on the neck 26 of the connector 22 may also engage the groove 434. For instance, the flange 36b of the neck 26 may engage the groove 434 prior to the flange 36a reaching the terminal end of the groove 434 as the connector 22 is distally advanced in the port 430. In turn, the connector 22 may remain aligned relative to the port 430 by interaction of the flange 36b of the neck 26 and the groove 434.

As the flange 36a of the sheath 34 engages the terminal end 440 of the groove 434, the connector 22 may continue to be advanced distally into the port 430. In turn, the engagement of the flange 36a with the terminal end 440 of the groove 434 may restrict further distal motion of the sheath 34. As such, continued advancement of the connector 22 may result in the sheath 34 moving proximally relative to the first connector portion 24 as the first connector portion 24 is advanced distally. That is, the first connector portion 24 may be advanced distally beyond the sheath 34. As such, the fill connection 40 may be moved distally relative to the fingers 38 such that the fill connection 40 is exposed. In addition, as the connector 22 is moved into a fully seated position relative to the port 430, the fill connection 40 may be disposed distally beyond the fingers 38 such that the fill connection 40 is exposed for engagement with a syringe to be filled as described in greater detail below.

Figure 11:
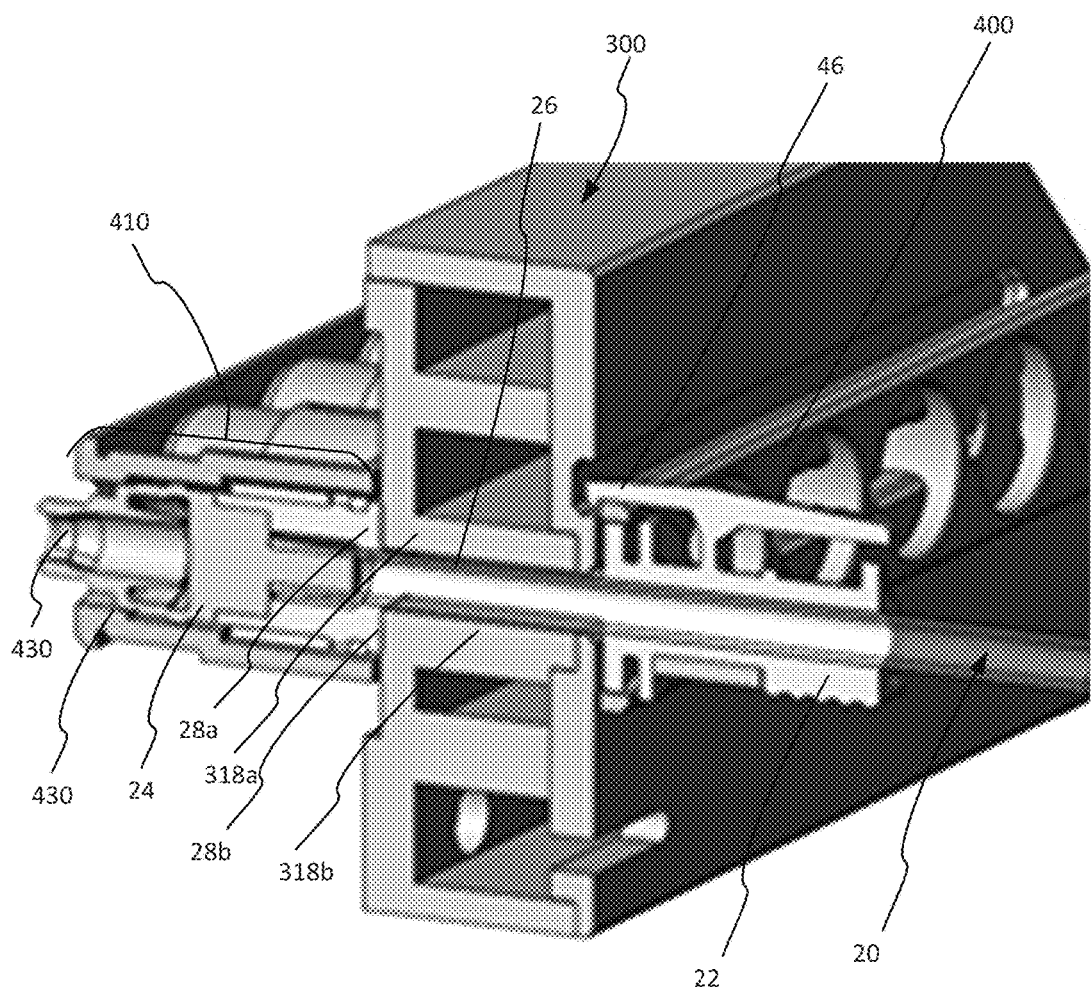
FIG. 11 depicts a cross sectional view of an embodiment of a port having a source fluid tubing set connector engaged therewith when away from the load position.

The connector 22 may be advanced distally in the port 430 until the neck 26 contacts the sheath 34 relative to which the connector 22 is advanced distally. In addition, the neck 26 may be aligned with the second portion 420 of the cartridge 400. In this regard, the planar body of the neck 26 may be coextensive with the bridge 432 such that the neck 26 and bridge 432 are aligned with the connector 22 is fully seated in the port 430. Further, upon full distal advancement of the connector 22 to fully seat the connector 22 in the port 430, the clip 46 may engage the cartridge 400 to assist in retaining the connector 22 in the fully seated position as shown in FIG. 11.

As addressed above, it may be advantageous to restrict engagement of an unengaged connector 22 to a port 430 or to restrict disengagement of an engaged connector 22 from a port 430 except for when the port 430 is disposed in a predetermined load position, which may be controlled by movement of the inlet block 200 relative to the track 300. This may prevent unintended or mistaken engagement and/or disengagement of a connector 22 from the inlet assembly 100. Accordingly, it may be appreciated that selective engagement and disengagement of the connector 22 of the source fluid tubing set 20 with a port 430 may be advantageous to reduce the potential of incorrectly engaging a source fluid tubing set 20 to the inlet assembly 10. This is especially true in this case of an inlet assembly 10 having a plurality of ports 430 for receiving source fluid tubing sets 20 from a plurality of source fluid receptacles. Accordingly, the inlet assembly 100 may include features that allow for selective engagement and/or disengagement of a connector 22 to a port 430, yet still allows for motion of the inlet block 200 engaged with a connector 22 in the first dimension along axis B-B.

Figure 6:
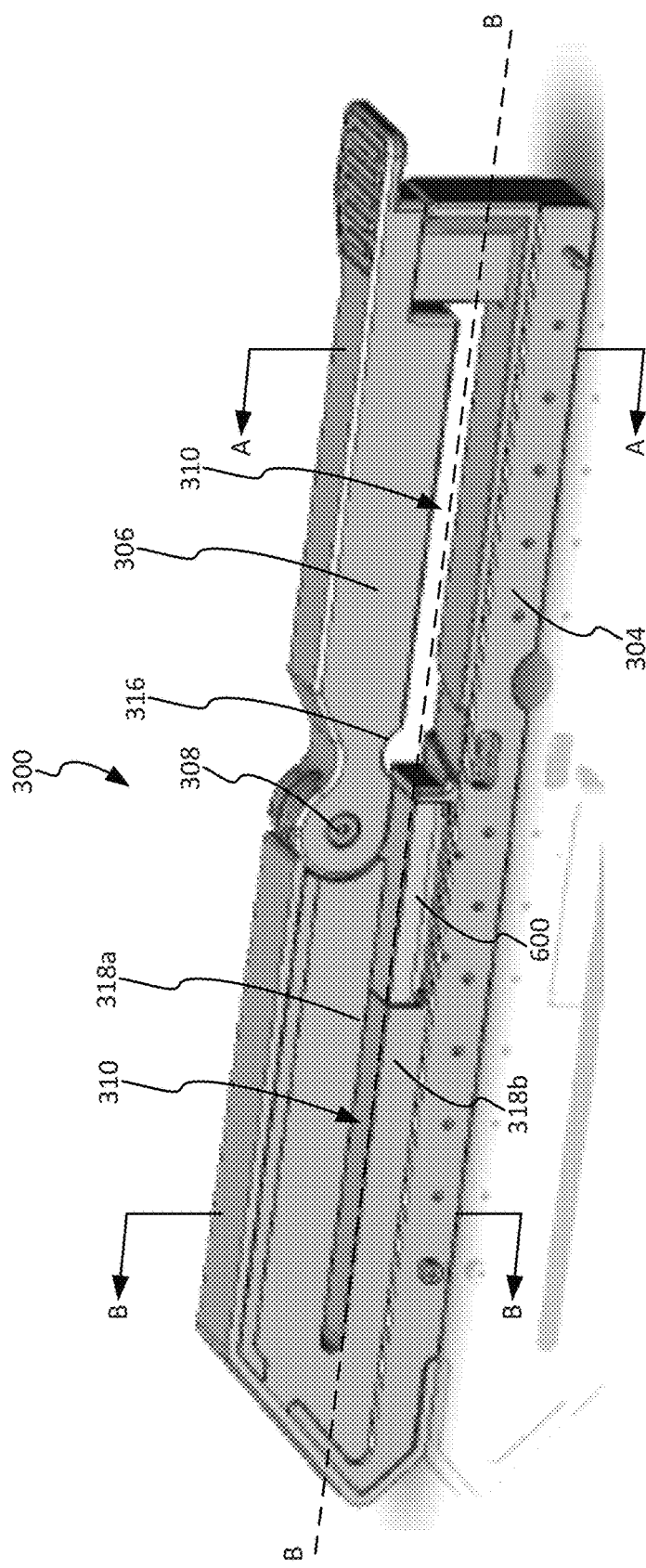
FIG. 6 depicts a perspective view of an embodiment of a track of a source fluid inlet assembly in isolation.

With further reference to FIG. 6, the track 300 shown in isolation. As may be appreciated, the slot 310 generally extends along the track 300 and is defined by both the first track member 304 and the second track member 306. The slot 310 may generally extend parallel to axis B-B. The second portion 420 of the cartridge 400 may be configured to engage the slot 310 to allow for linear movement of the cartridge 400 within the slot 310 along substantially the entire length of the slot 310 as the cartridge 400 is moved by the shuttle 212. However, as addressed above, the cartridge 400 may be prevented from being removed from the shuttle 212 (e.g., by mechanical interference) except for when the shuttle 212 is in the cartridge load position and the second track member 306 is in the open position. The interface of the cartridge 400 relative to the track 300 is described in greater detail below.

The track 300 may include a recess 316 along a rail 318 of the slot 310 whose shape may correspond to at least a portion of the cross sectional area of the port 430 of the cartridge 400. That is, with further reference to FIG. 7B, at least one rail 318 of the the slot 310 may extend relative to the port 430 of the cartridge 400 except in a position in which a port 430 is aligned with the recess 316 of the track 300. For example, port 430' in FIG. 7B is aligned with the recess 316 such that the full cross sectional area of the port 430 is exposed. However, the other ports 430 depicted are at least partially blocked by the rail 318.

As such, the rail 318 of the track 300 that extends relative to the ports 430 may block engagement and disengagement of a connector 22 of source fluid tubing set 20 with a port 430. For instance, with further reference to FIGS. 25A and 25B, FIG. 25A depicts a cross sectional view taken along A-A in FIG. 6 with a cartridge 400 disposed in place relative to the slot 310. FIG. 25B depicts a cross sectional view taken along B-B in FIG. 6 with a cartridge disposed relative to the slot 310. As such, in FIG. 25A, a first rail 318a may extend into a first channel 422a of the cartridge 400, thus blocking at least a portion of the cross sectional area of the port 430 (i.e., providing a mechanical interference to the advancement of the connector 22 in the port 430). In the position shown in FIG. 25A, the second rail 318b may not be provided to provide for clearance for engagement and disengagement of the cartridge 400 with the aperture 210 of the shuttle 212 as described above. However, as shown in FIG. 25B, the second rail 318b may extend into the second channel 422b such that the rail 318b may extend relative to the cross sectional extent of the port 430 as well to at least partially block (i.e., cause mechanical interference) the cross sectional area of the port 430.

In turn, in the event that a connector 22 is not engaged with the port 430, engagement may not be possible when the cartridge 400 is disposed away from the load position corresponding to the recess 316 as shown in FIG. 25A or 25B. That is, if a connector 22 were attempted to be introduced into the port 430, the first connector portion 24 would contact and be prevented from further distal advancement by way of mechanical interference with the rail 318a extending in the channel 422a (and/or rail 318b extending into channel 422b) relative to the port 430. Furthermore, in an instance where a connector 22 is engaged with the port 430, the neck 26 may be aligned with the bridge 432, which are both disposed in the slot 310 for linear motion in the first dimension (i.e., along axis B-B, which extends into and out of the page as depicted in FIGS. 25A and 25B). That is, the neck 26 and bridge 432 may allow for positioning of the cartridge 400 by the inlet block 200 along the length of the slot 310 extending parallel to axis B-B. However, should the connector 22 attempt to be withdrawn proximally from the port 430 when in the position show in FIG. 25A or 25B, a first shoulder 28a (and/or a second shoulder 28b) of the connector 22 would engage the first rail 318a (and/or second rail 318b) which is disposed in the channel 422a (and/or channel 422b) to prevent proximal movement of the connector 22 from the port 430. This is further depicted in FIG. 11.

However, an aligned port 430' may be aligned with the recess 316 of the track 300 such that the aligned port 430' may not be blocked by the track 300. In this regard, the port 430' may be capable of having the connector 22 of the source fluid tubing set 20 being engaged and disengaged with the port 430'. In this regard, the port 430' may be disposed in a load position such that the port 430' is aligned with the recess 316 and is free to be engaged with or disengaged with a connector 22 of a source fluid tubing set 20. A visual indication may be provided to the user to indicate the location of the port 430' when in the load position. For instance, the track 300 may comprise a marking or other visual indication of location of the port 430' when in the load position. Furthermore, a light or other visual indicator may be provided that may, for example, illuminate the cartridge 400 and/or port 430' when in the load position.

Figure 8:
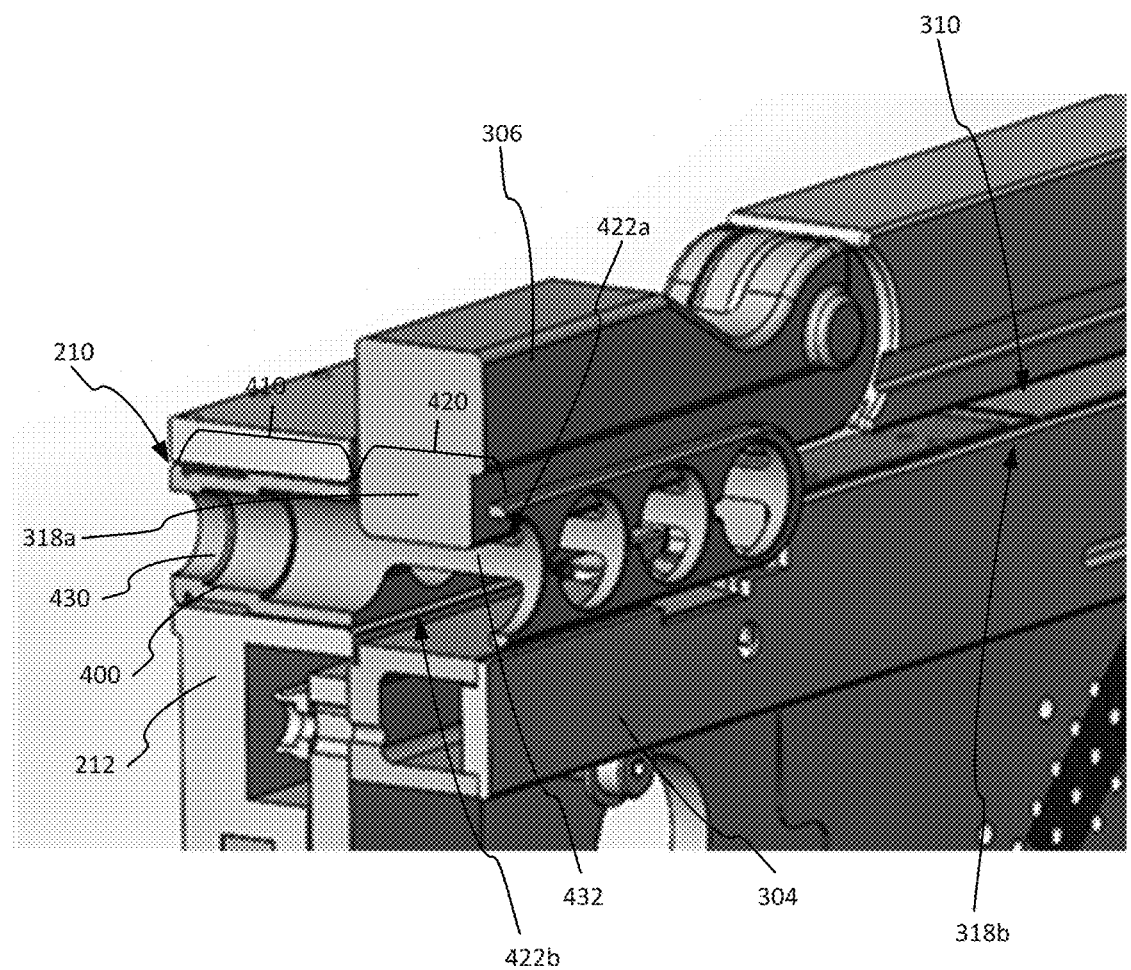
FIG. 8 depicts a cross sectional view of an embodiment of a port in a position away from the fill position.
Figure 26:
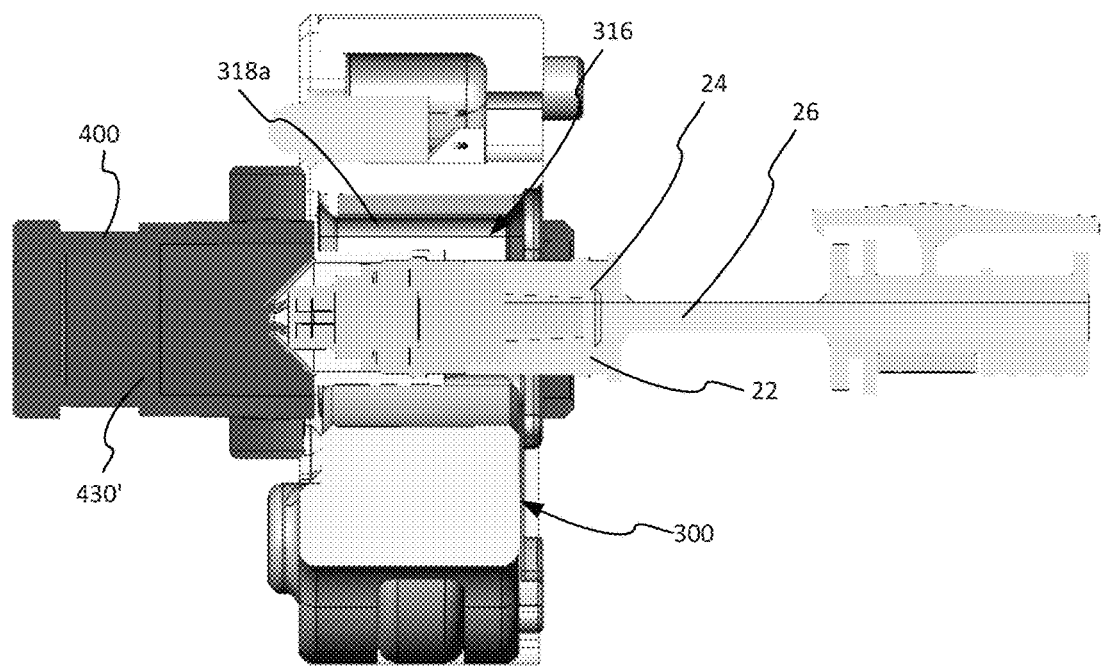
FIG. 26 depicts a cross sectional view of an embodiment of a cartridge engaged with a track to position a port in a fill position for engagement with a connector of a source fluid tubing set.

With further reference to FIG. 26, which depicts a cross sectional view of a port 430' of a cartridge 400 in a load position, as the port 430' is aligned with the recess 316 in the rail 318a, the cross sectional area of the port 430' may be unobstructed. In turn, a connector 22 may be freely advanced distally or proximally relative to the port 430' such that the first connector portion 24 is allowed to travel past the second portion 420 of the cartridge 400 to engage the first portion 410 of the cartridge 400. In this regard, the connector 22 may be advanced distally and become fully seated as described above. Furthermore, as the neck 26 may be aligned with the bridge 432 of the second portion 420, once the connector 22 is fully seated in the load position, the cartridge 400 may be moved away from the load position in the first dimension along axis B-B such that the neck 26 and the bridge 432 are disposed within the slot 310 to allow for the motion of the inlet block 200 in the first dimension along axis B-B. For instance, with returned reference to FIG. 8, the bridge 432 of the connector may be disposed within the slot 310 between one or more rails 318 of the slot 310. In this regard, the bridge 432 may move relative to the one or more rails 318 when the cartridge 400 is moved in the first dimension by the shuttle 212.

Figure 12:
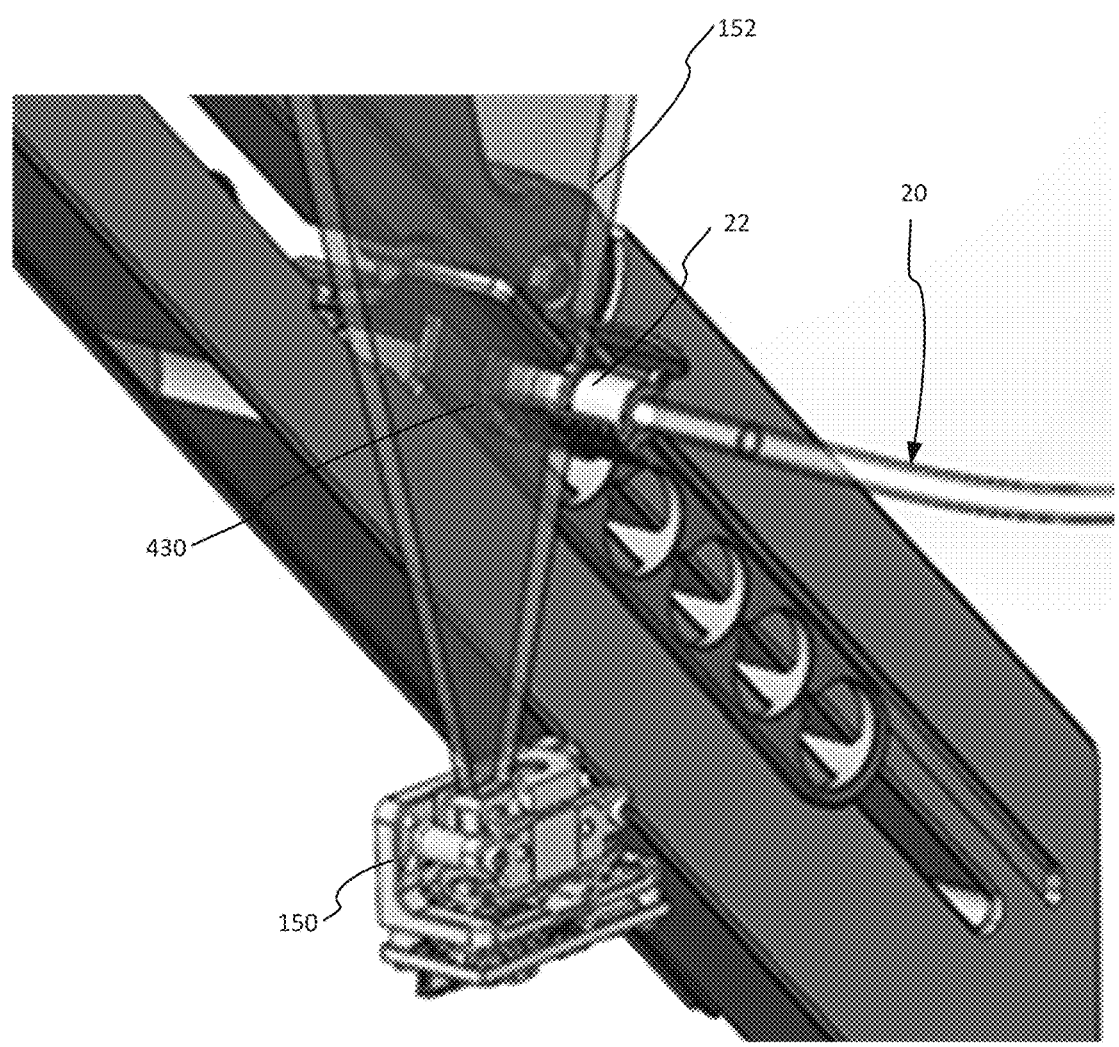
FIG. 12 depicts an embodiment of a reader disposed relative to a track for reading an indicia disposed on a connector.

With further reference to FIG. 12, the inlet assembly 100 may include a reader 150 that may be disposed such that a field-of-view 152 of the reader 150 extends relative to the connector 22 once the connector 22 has been engaged with the port 430. As discussed above, the connector 22 may include machine-readable indicia 36 (e.g., on the second connector portion 44). The indicia 36 may be disposed within the field-of-view 152 of the reader 150 after the connector 22 has been engaged with a port 430. As such, verification of the tubing set 20 may be performed by the reader 150 identifying the tubing set 20 by way of the indicia disposed on the connector 22 disposed within the field-of-view 152 of the reader 150. Specifically, the reader 150 may read the machine readable indicia of the connector 20 to verify, for example, an identity of the tubing set 20. The port 430 may be moved in the first dimension along axis B-B from the load position to a read position to dispose the indicia on the connector 22 within the field-of-view 152 of the reader 150.

Figure 13:
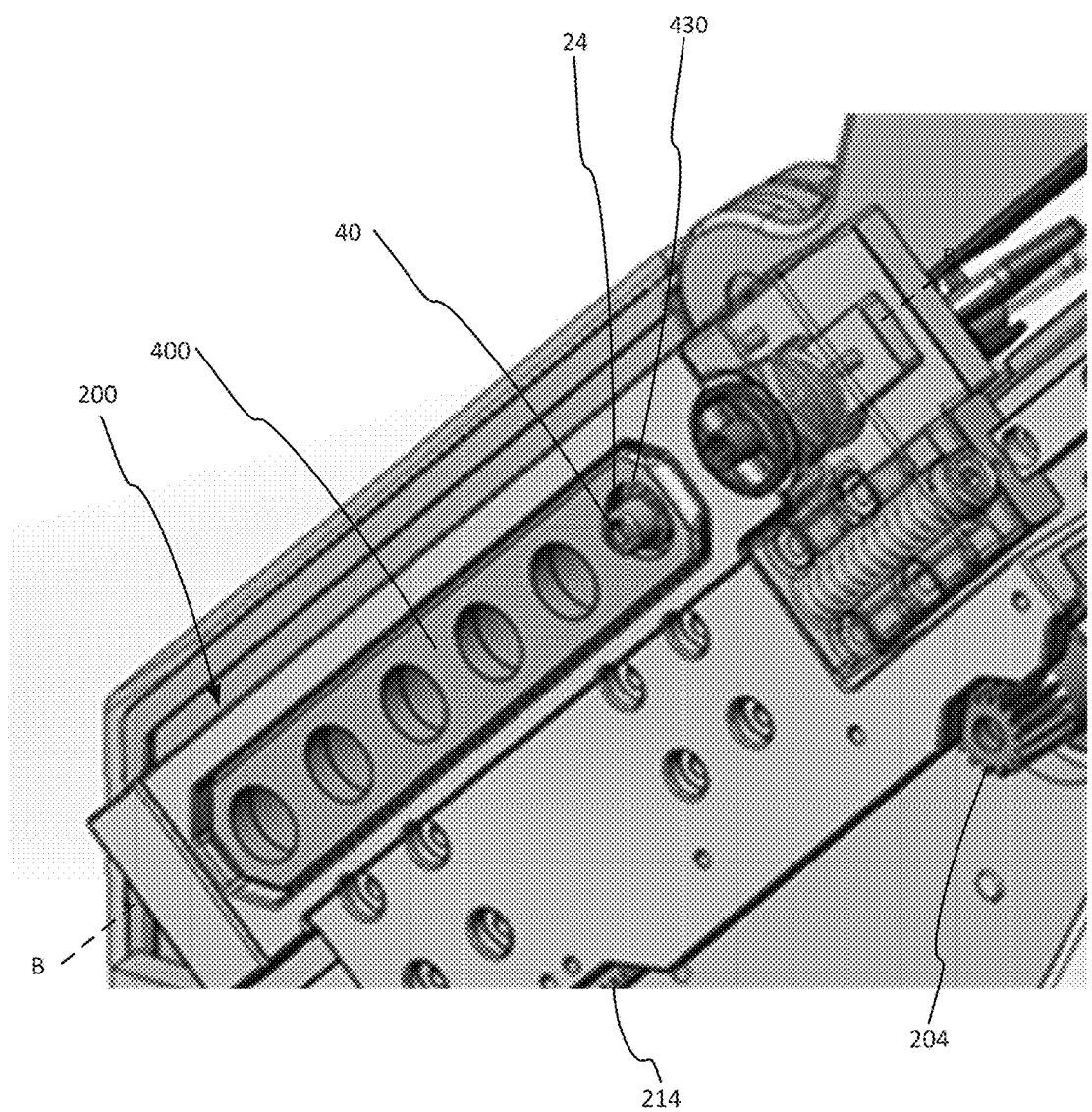
FIG. 13 depicts an embodiment of a source fluid inlet assembly having a source fluid tubing set engaged with a port.
Figure 14:
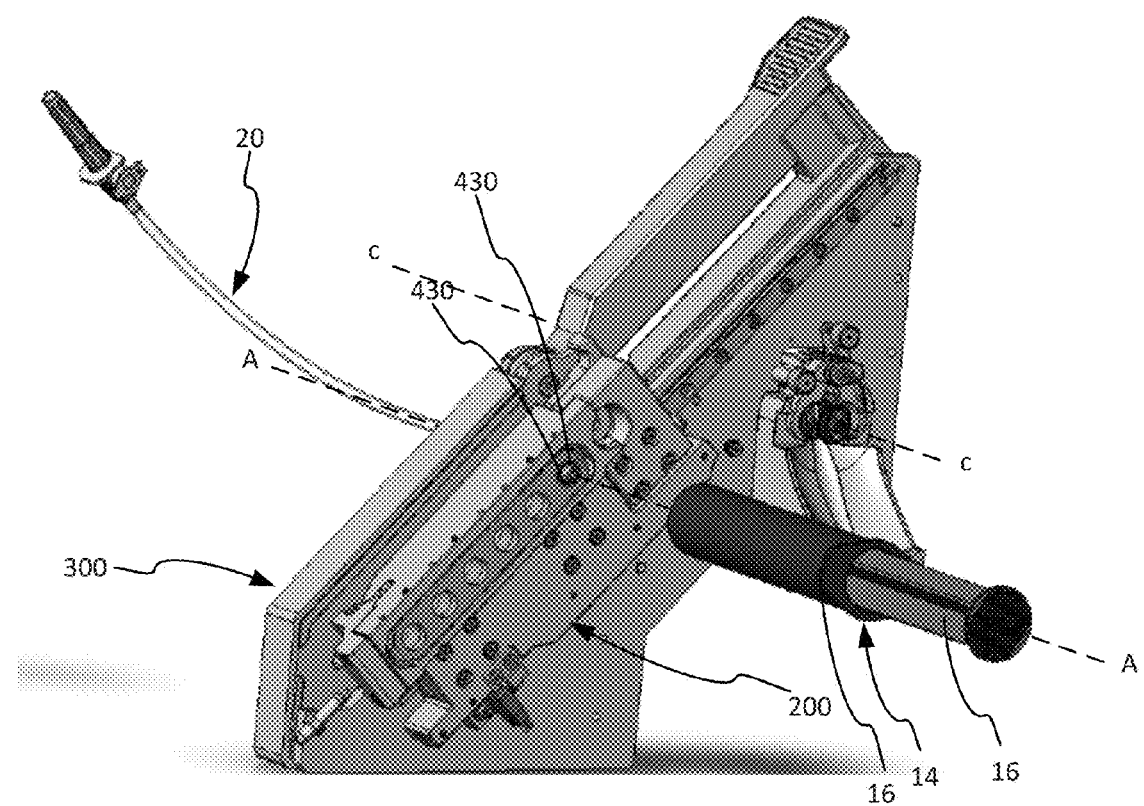
FIG. 14 depicts an embodiment of a source fluid inlet assembly with an inlet block disposed in a fill position relative to a syringe.

With further reference to FIGS. 13 and 14, the inlet block 200 is shown from the perspective of an interior of the automated filling device 10 such that the fill connection 40 of the port 430 may be disposed for engagement with a syringe to establish fluid communication between the port fill connection 40 and the syringe 14. As may be appreciated, the fill connection 40 of the connector 22 may facilitate a fluid interconnection interface with a syringe 14 that may be manipulated by the automated syringe filling device 10. The structure for manipulating the syringe 14 is not shown for clarity, but any structure that may move the syringe 14 that is aligned with a predetermined axis A-A along the predetermined axis A-A may be employed without limitation.

Accordingly, the inlet block 200 may move along the track 300 to dispose the port 430 engaged with the connector 22 of a source fluid tubing set 20 into a fill position. Specifically, in the fill position, the port 430 (e.g., the fill connection 40 engaged with the port 430) may be aligned with the predetermined axis A-A along which a syringe 14 is also axially aligned. The automated filling device 10 may be operative to move the syringe 14 linearly along the axis A-A. In this regard, the syringe 14 may be advanced relative to the connector 22 disposed in the port 430 to establish fluid communication between the syringe 14 and the connector 22. Accordingly, the automated filling device 10 may be operative to withdrawal a plunger 16 of the syringe 14 relative to the barrel 18 so as to draw fluid from the source fluid tubing set 20 into the syringe 14 upon establishing fluid interconnection between the syringe 14 and the connector 22.

Additionally, it may be advantageous to monitor the tubing set 20 to, for example, monitor the contents of the tubing set 20 in connection with priming and/or filling operations. In this regard, traditional bubble detection sensors often require placement of the tubing 20 to be monitored between specific sensor elements of the sensor. However, and especially in the context of a source inlet assembly 100 having a plurality of ports 430, placement of the tubing set 20 relative to (e.g., between) specific sensors with reliability may be difficult or complex beyond economic feasibility. As such, the source inlet assembly 200 may be configured to allow for monitoring of a tubing set 20 without requiring specific placement of the tubing set 20 between specific sensor elements of a bubble detection sensor.

Rather, the source inlet assembly 100 may include a single plate capacitive bubble detection sensor 600. With reference to FIGS. 4 and 6, the single plate capacitive sensor 600 may be arranged relative to the track 300 such that the sensor 600 may comprise at least a portion of a rail 318. In turn, the sensor 600 may have a sensor portion arranged adjacent to the slot 310 such that a portion of the connector 22 may be disposed relative to the sensor portion of the sensor 22. Specifically, as described above, the neck 26 of the connector 22 may allow a portion of the tube 42 to extend beyond the planar extent of the neck 26. As the neck 26 may be disposed adjacent to the rail 318b in the fill position, the sensor 600 may be disposed in the channel 422b adjacent to the exposed tubing 42 at the neck 26. In this regard, the tubing 42 in the neck 26 may be disposed in close proximity to the sensor 600 when the port 430 is disposed in the fill position.

As mentioned briefly above, the sensor 600 may be disposed on a single side of the tubing 42. That is, the single plate capacitive sensor 600 may comprise a capacitive sensor with a single sensor portion that is operative to sense a parasitic capacitance relative to an adaptive baseline to determine a change in the material in the tubing 42. In turn, the sensor 600 may be utilized in a priming operation to determine when the contents of the tubing 42 changes from air to liquid. Furthermore, the sensor 600 may be used for bubble detection during a filling operation to detect if air is present in the tubing 42. Furthermore, given the parasitic capacitance detected by the sensor 600 may be based on a dielectric constant of the material in the tube 42, and different materials may have different dielectric constants, the sensor 600 may be operative to detect or assist in confirm a contents (e.g., a given material) in the tube 42.

In particular, the use of a single plate capacitive sensor 600 may allow for simple positioning of tubing 42 to be monitored relative to the sensor 600. That is, upon movement of the inlet block 200 into the fill position to dispose the port 430 relative to the predetermined axis A-A, the tubing 42 at the neck 26 may be disposed in position relative to the sensor 600 so that the tubing 42 may be monitored by the sensor 600 without further manipulation or positioning of the tubing 42. In turn, as any given port 430 (e.g., in the case of a cartridge 400 with a plurality of ports 430) is disposed in the fill position, the tubing 42 corresponding to the given port 430 may be in position relative to the sensor 600 simply upon disposing the port 430 in the fill position without further manipulation of the tubing 42. As such, different ones of a plurality of ports may be easily moved into position relative to the sensor 600 to monitor the tubing 42.

Figure 15:
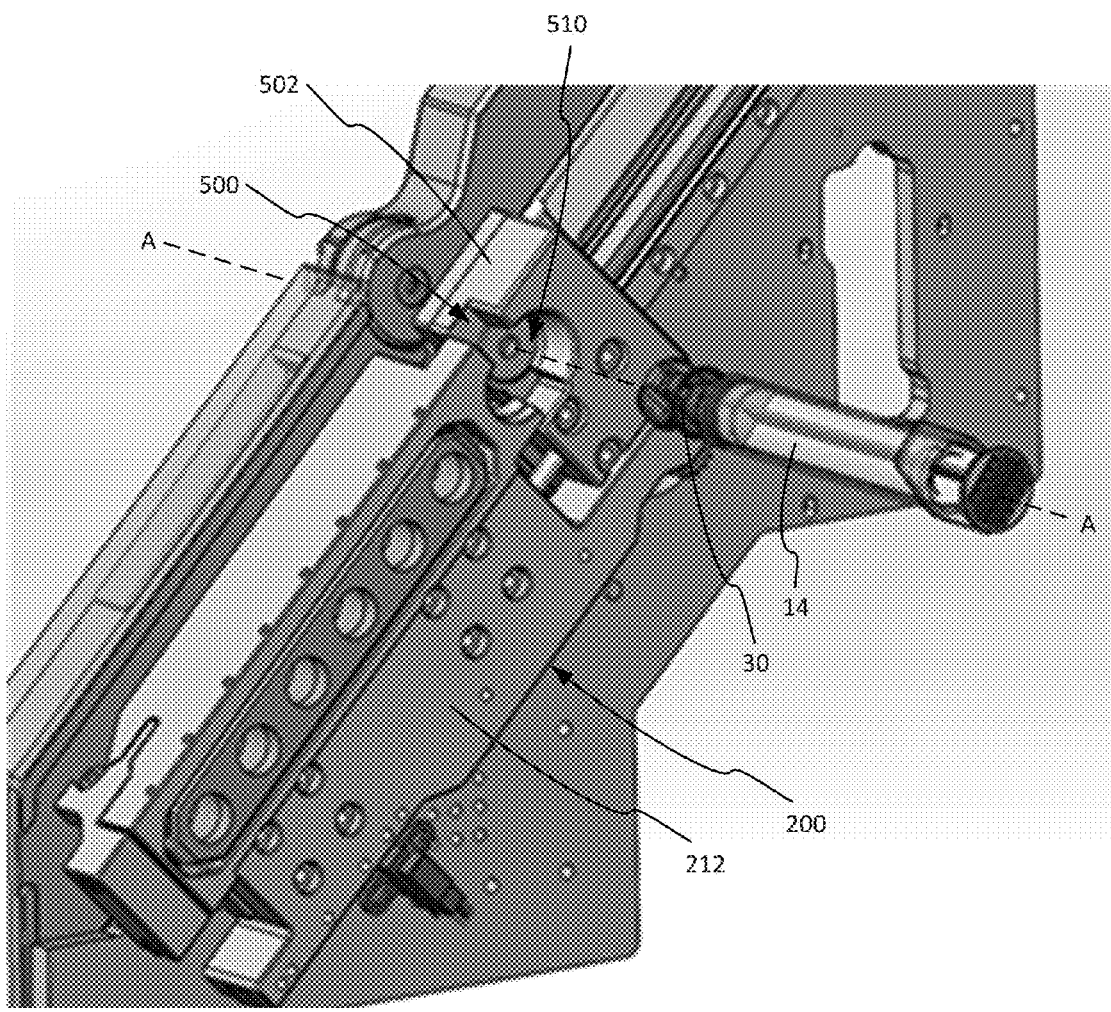
FIG. 15 depicts an embodiment of a source fluid inlet assembly with an inlet block in a decapping position with a cap retention cavity in an open position.
Figure 16:
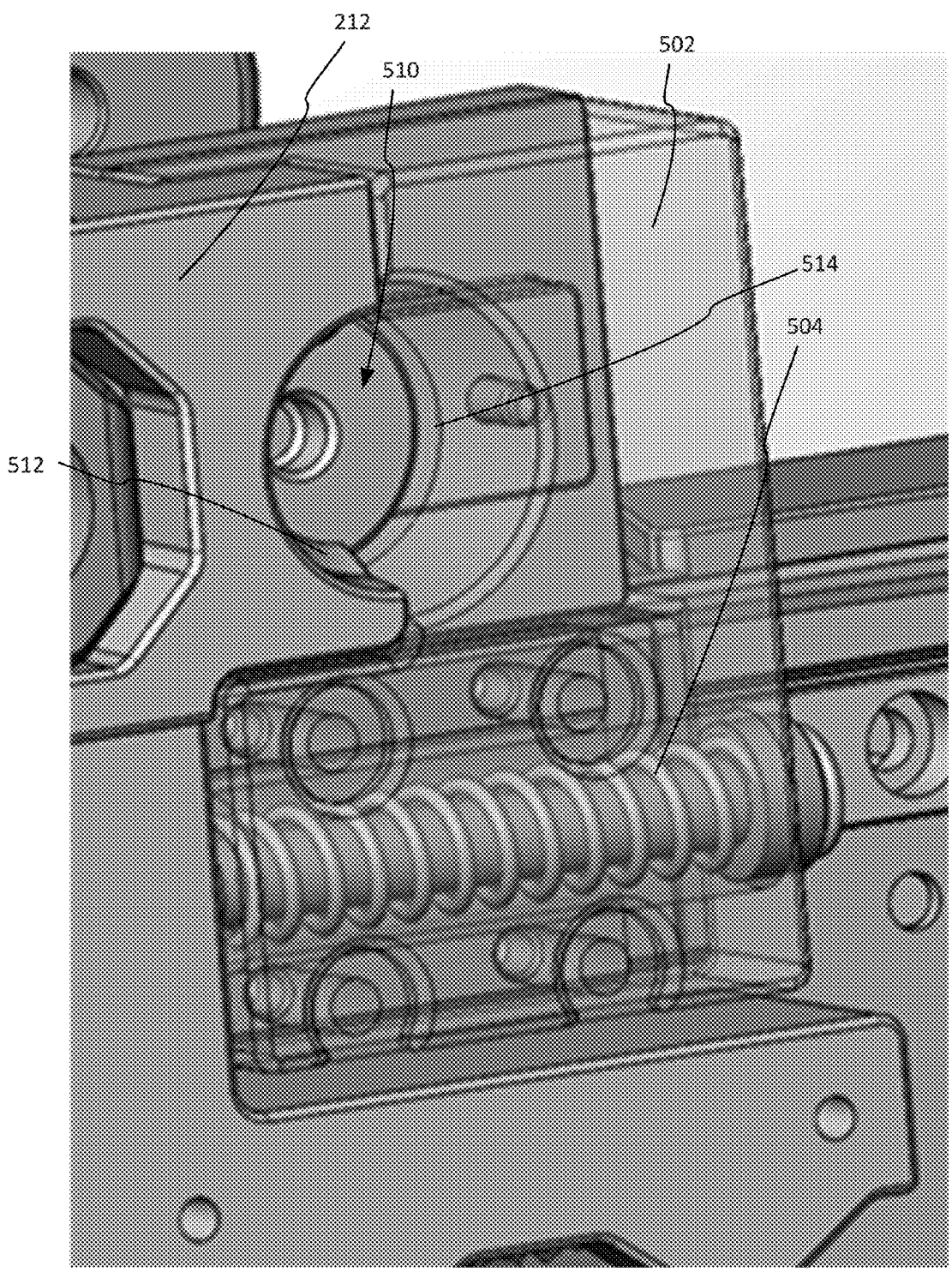
FIG. 16 depicts a perspective view of an embodiment of a cap retention cavity.

With further reference to FIG. 15, it may be appreciated that a syringe 14 may include a cap 30 disposed on the syringe 14 prior to filling. For instance, the syringe 14 may be introduced into the automated filling device 10 with a cap 30 thereon. Alternatively, the automated filling device 10 may cap the syringe 14 in connection with the operation of the automated filling device 10. In this regard, the cap 30 may be removed from the syringe 14 prior to moving the port 430 into the fill position to engage the syringe 14 with the connector 22 for filling of the syringe 14.

In this regard, the inlet block 200 may include a decapping mechanism 500 that may be operative to engage and retain a cap provided on a syringe in connection with the filling of the syringe. Specifically, and with reference to FIGS. 15-22, the decapping mechanism may include a cap retention cavity 510. The cap retention cavity 510 may be disposed between an open position in which the cap retention cavity 510 may accept a cap 30 and a closed position in which a cap 30 disposed in the cap retention cavity 510 may be retained. As will be discussed below, the decapping mechanism 500 may be operative to engage, allow for removal, and retain a cap 30 from a syringe 14. In turn, the syringe 14 may be decapped, filled, and recapped utilizing the decapping mechanism 500.

Figure 17:
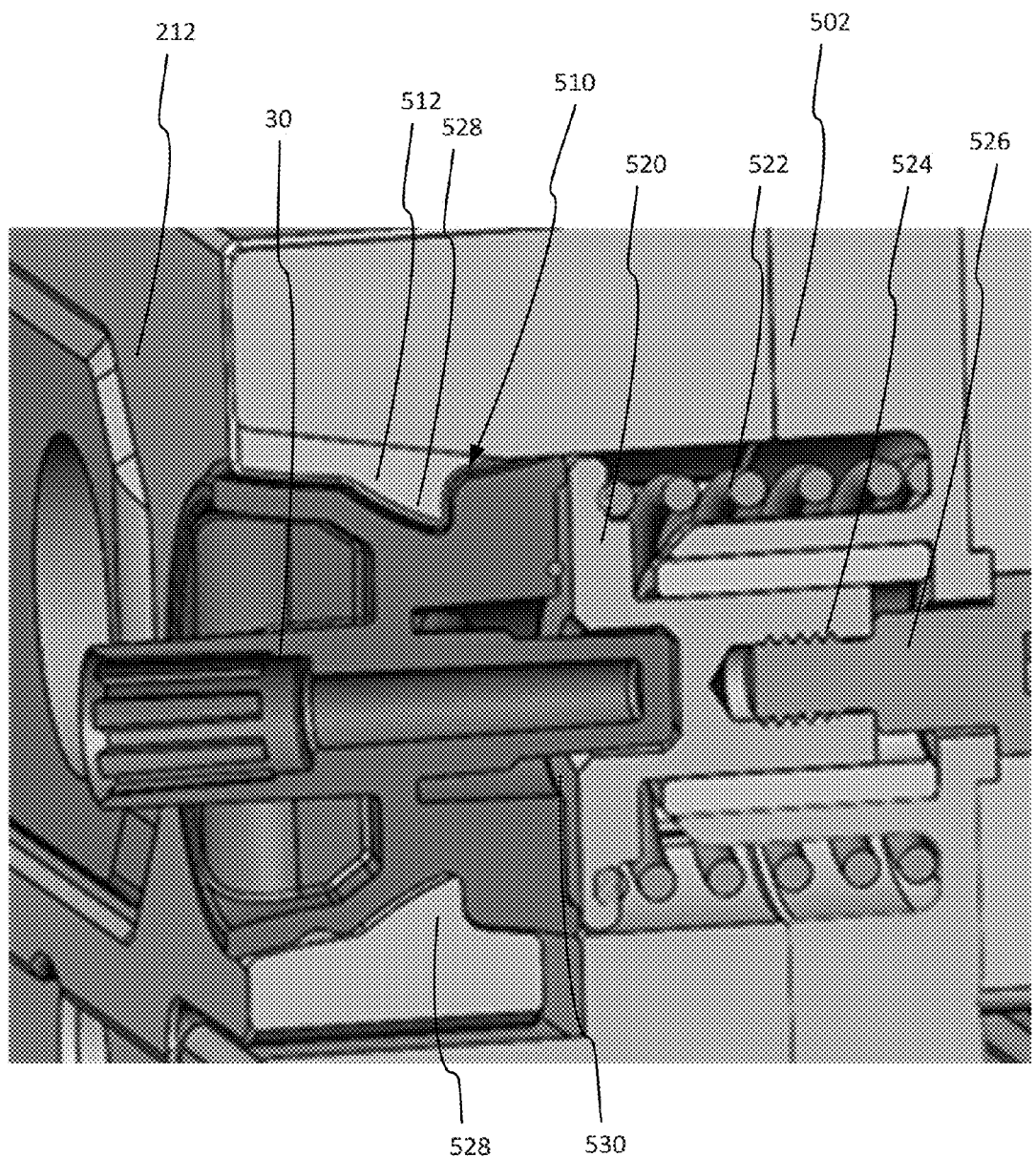
FIG. 17 depicts a cross sectional view of a cap retention cavity having a cap retained therein.

The slide 502 may be engaged with the shuttle 212. Specifically and with further reference to FIG. 16, the slide 502 may be attached to the shuttle 212 by a spring-loaded shoulder bolt 204. The spring-loaded shoulder bolt 204 may bias the slide 502 into contact with the shuttle 212. In this regard, the shuttle 212 may define a first portion 512 of the cap retention cavity 510. The slide 502 may define a second portion 514 of the cap retention cavity 510. With further reference to FIG. 17, the cap 30 is disposed within the cap retention cavity 510. As may be appreciated, the first portion 512 and/or second portion 514 may include barbs 528 or other extensions that may engage corresponding contours of the cap 30 to retain the cap 30 within the retention cavity 510.

In this regard, the cap 30 may be engaged by the cap retention member 310 when in a closed position such that when a syringe 14 is withdrawn relative to the inlet block 200, the cap 30 may be retained in the cap retention cavity 510. In this regard, as shown in FIG. 15, the cap retention cavity 510 may be disposed in a decapping position such that the cap retention cavity 510 may be aligned with the predetermined axis A-A along which the syringe 14 may be aligned. Once in the decapping position, the slide 502 may be constrained to prevent further linear motion of the slide 502 past the decapping position. For example, further reference to FIG. 19, the slide 502 may include a tab 516 that is engageable with a stop 518 disposed on the track 300. The tab 516 may engage stop 518 such that the slide 502 cannot progress linearly beyond the decapping position in the first dimension.

Figure 20:
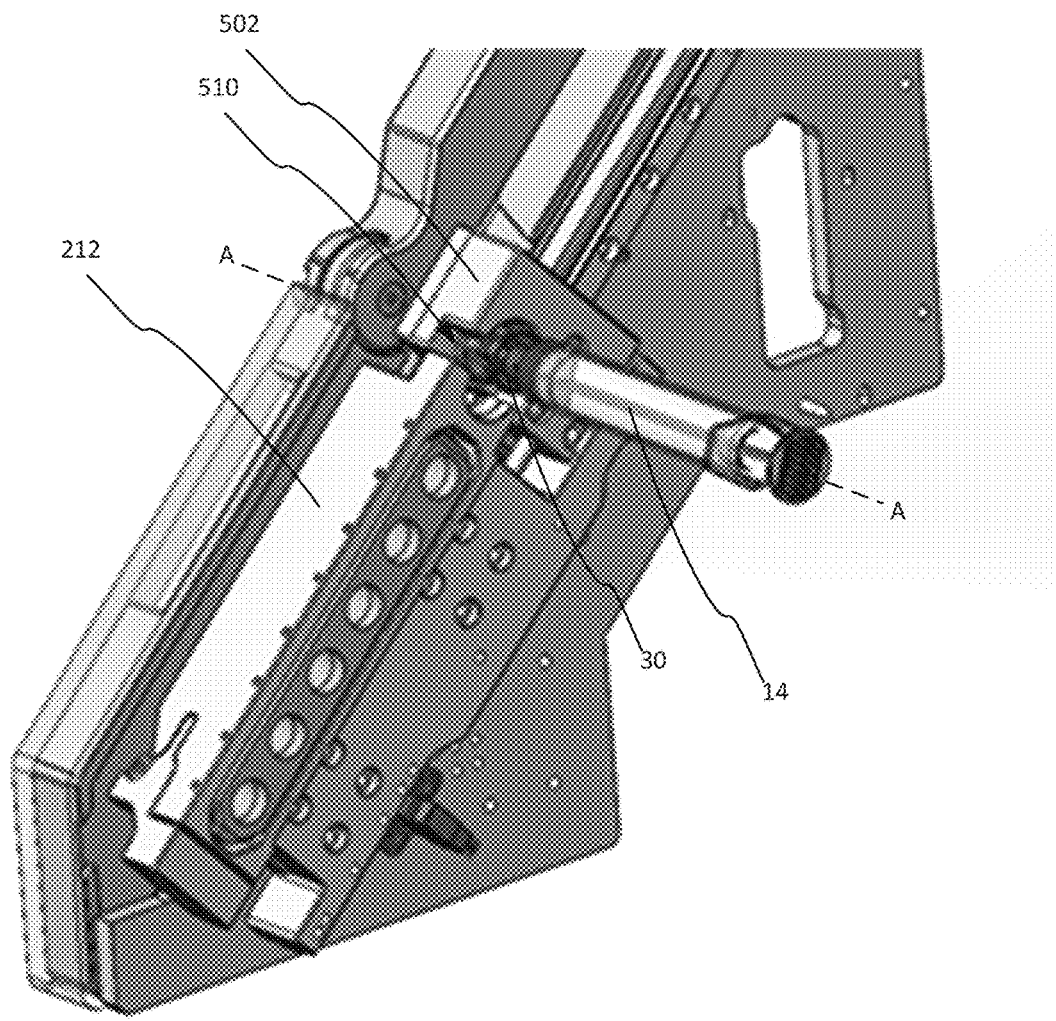
FIG. 20 depicts a perspective view of a source fluid inlet assembly with an inlet block disposed to open a cap retention cavity with a capped syringe in position relative thereto.

However, with returned reference to FIG. 15, the shuttle 212 may be further advanced in the first dimension beyond the decapping position. The further advancement of the shuttle 212 relative to the slide 502 which is constrained from further linear movement in the first dimension beyond the decapping position may result in the biasing force imparted by the spring-loaded shoulder bolt 504 to be overcome such that the shuttle 212 is separated from the slide 502. In this regard, the first portion 512 and the second portion 514 may undergo relative movement to dispose the cap retention cavity 510 in an open position as shown in FIG. 15. In turn, the syringe 14 may be advanced along the predetermined axis A-A such that the cap 30 is disposed within the cap retention cavity 510 as shown in FIG. 20.

While the foregoing arrangement of the slide 502 and shuttle 212 may be advantageous as the opening and closing of the cap retention cavity 510 may be based on movement of the inlet block 200 along axis B-B (e.g., by operation of the motor 202), other arrangements may be provided to position the cap retention cavity 510 between the open and closed positions. For instance, an actuator may be provided to move the slide 502 relative to the shuttle 212. Such an actuator may include a solenoid, pneumatic cylinder, additional motor, or other appropriate actuator. Further still a specifically arranged cam surface may be provided to facilitate opening and closing of the cap retention cavity 510.

Figure 18:
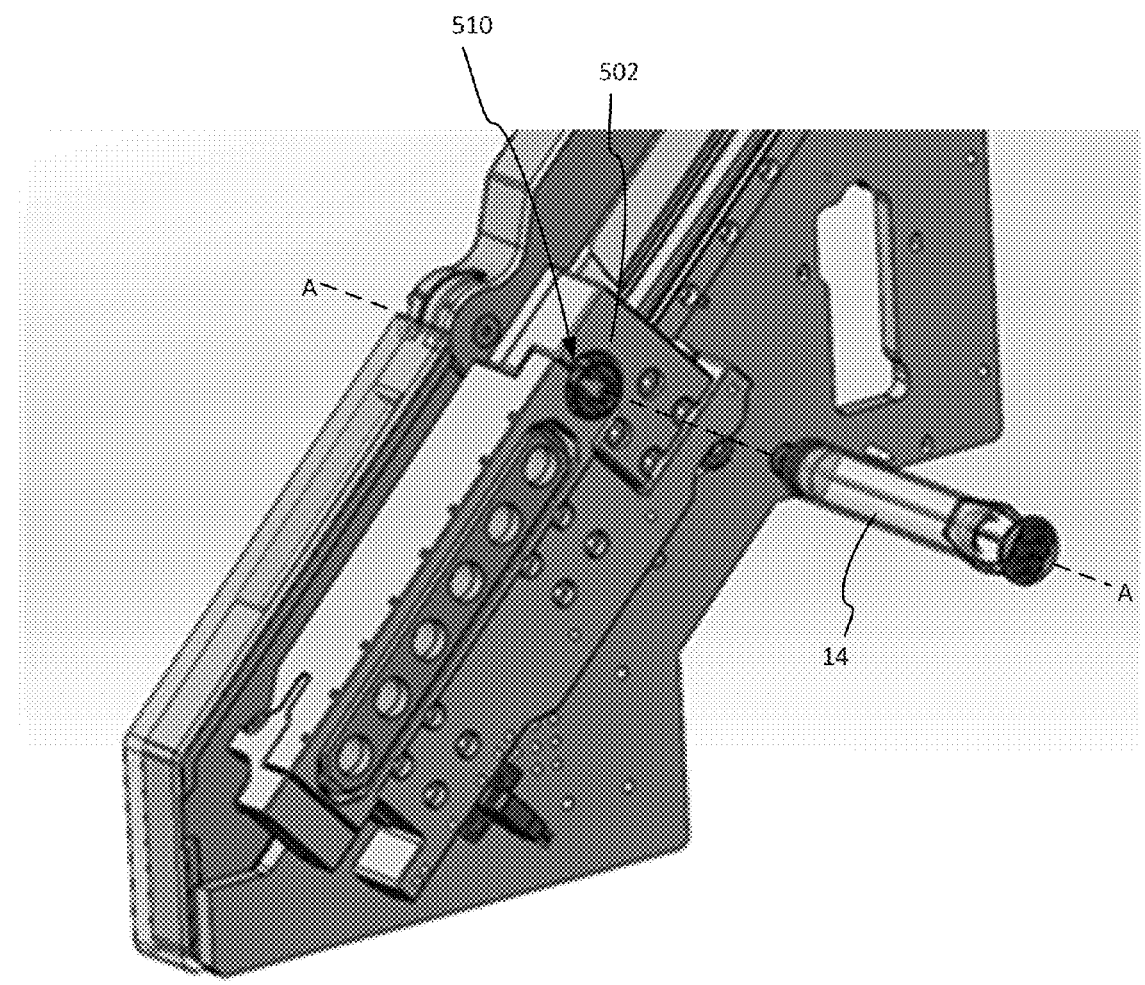
FIG. 18 depicts a perspective view of an embodiment of a source fluid inlet assembly with an inlet block having a cap retained in a cap retention cavity and disposed relative to a syringe.
Figure 19:
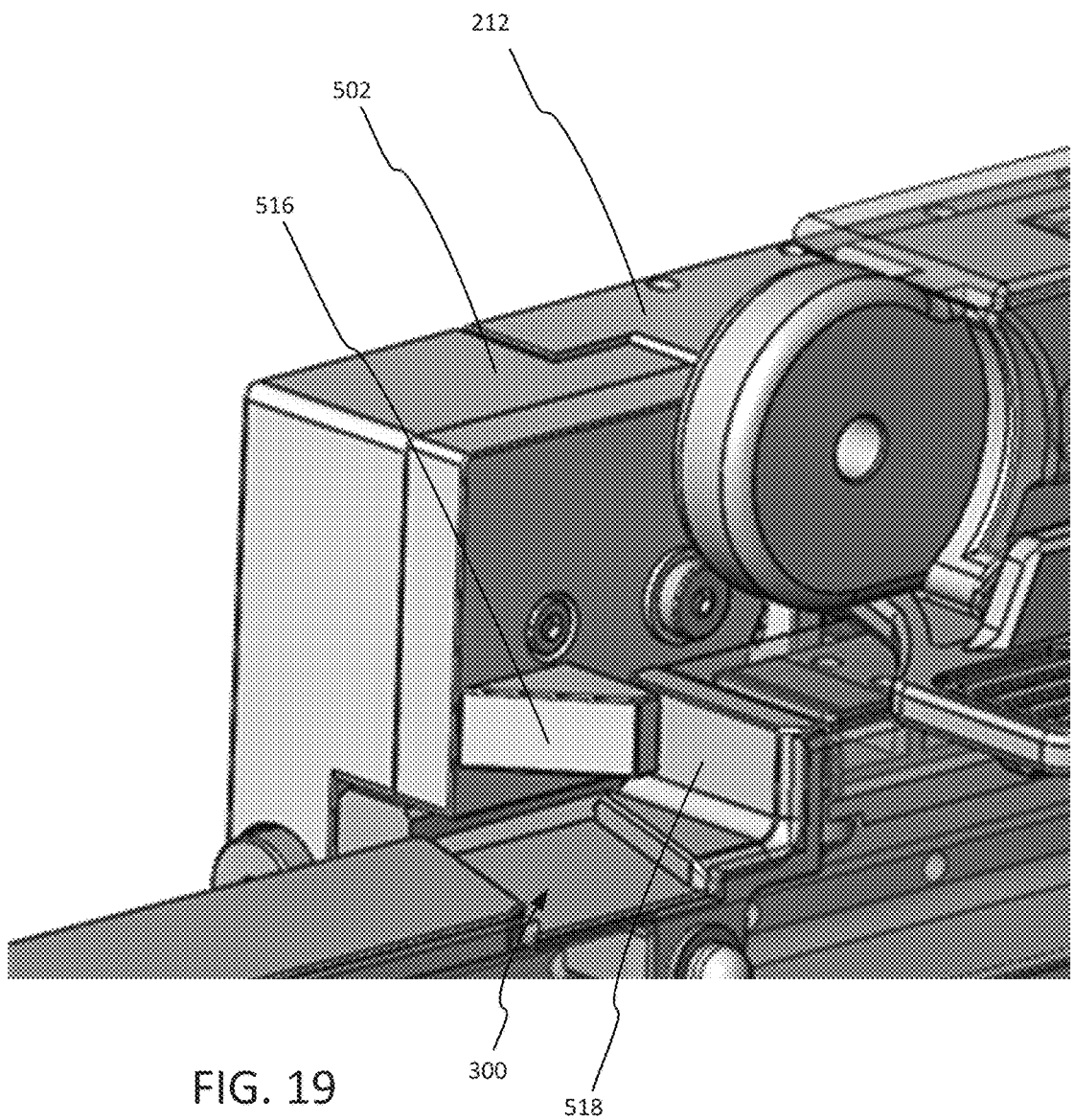
FIG. 19 depicts a perspective view of an embodiment of a tab and stop associated with shuttle and slide comprising a decapping mechanism for use in moving a cap retention cavity between an open and closed position.
Figure 21:
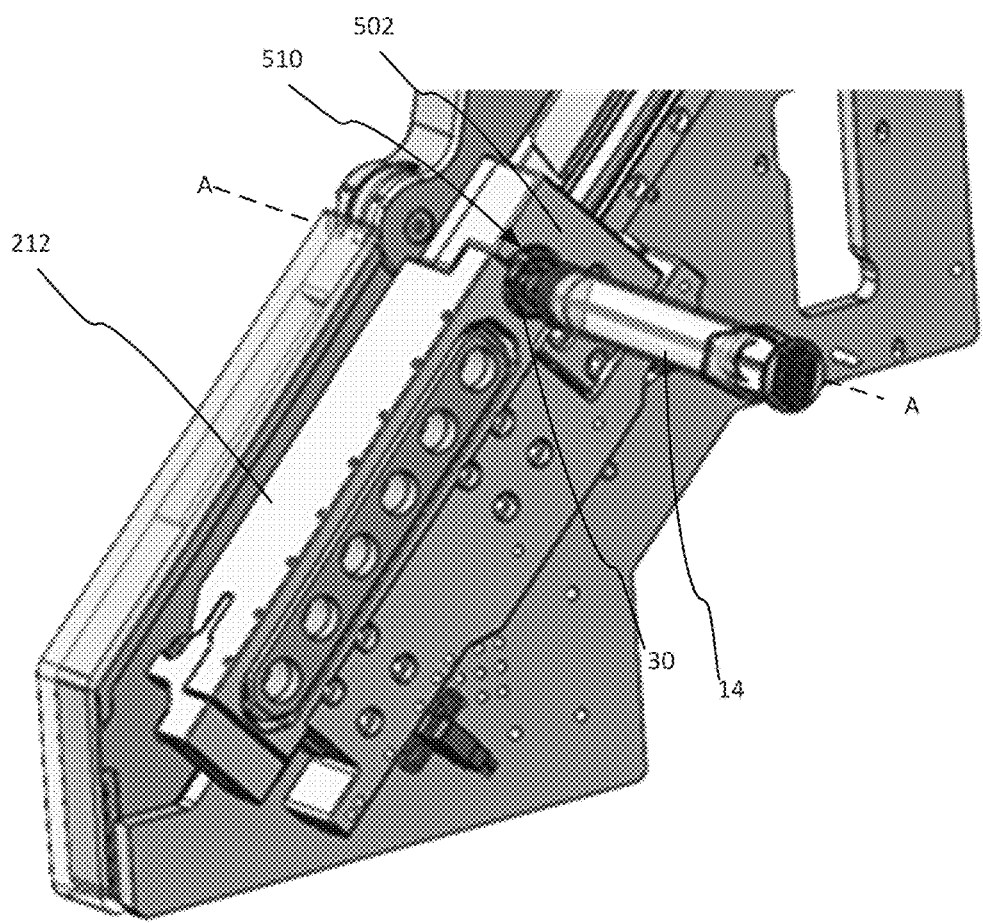
FIG. 21 depicts a perspective view of a source fluid inlet assembly with an inlet block disposed to close a cap retention cavity with a capped syringe in position relative thereto.

The shuttle 212 may be returned to the cap retention position such that the first portion 512 and the second portion 514 of the cap retention cavity 510 are returned to the closed position to engage the cap 30 as shown in FIGS. 17 and 21. The syringe 14 may be moved away from the inlet block 200 along the predetermined axis A-A while the cap 30 is engaged in the cap retention cavity 510 such that Is removed from the syringe 14 as shown in FIG. 18.

Figure 22:
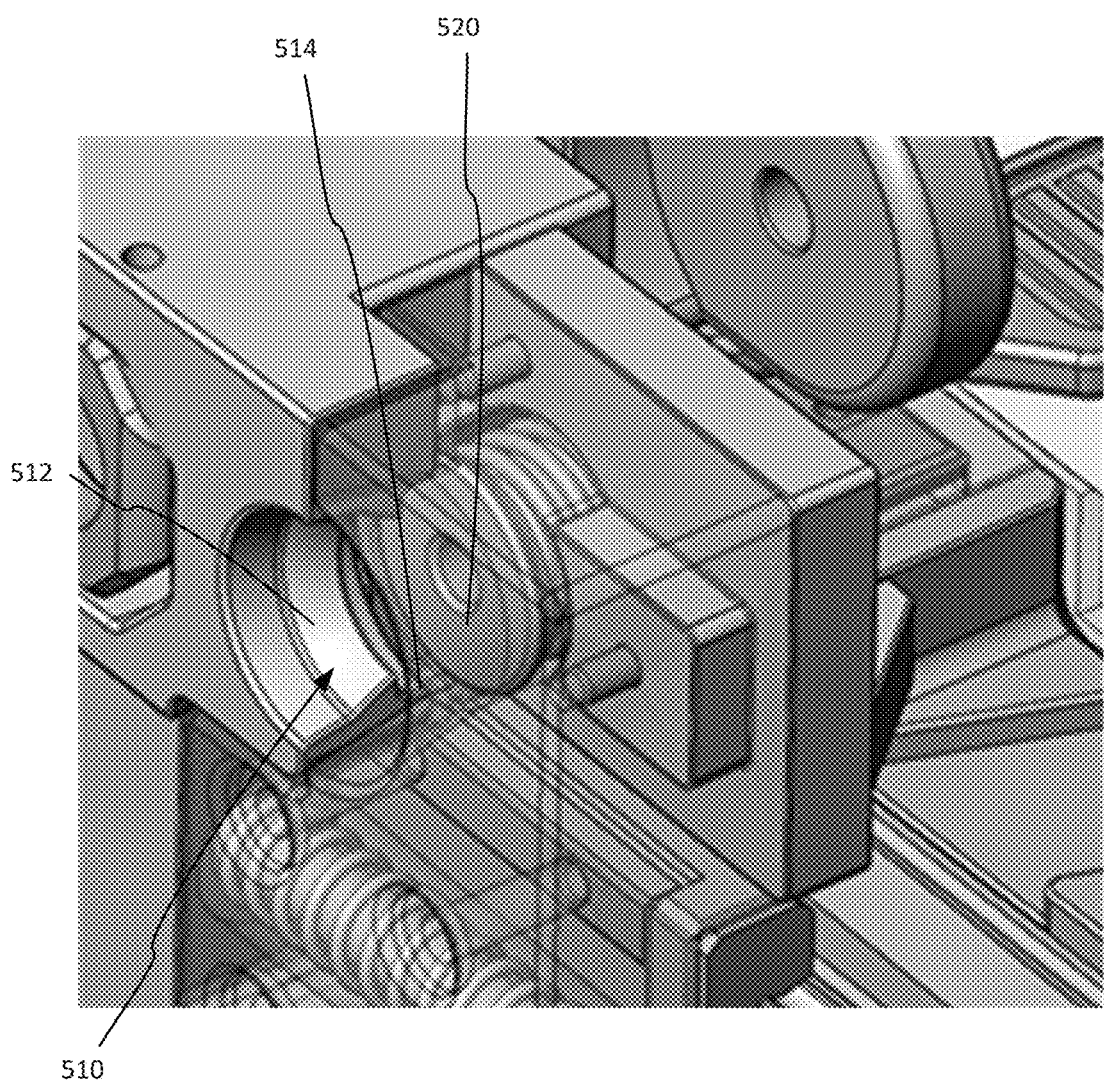
FIG. 22 depicts a perspective view of an embodiment of a cap retention cavity.

The inlet block 200 may be moved to the fill position such that the decapped syringe 14 may be engaged with the connector 22 disposed in the port 430 of the inlet block 200. Upon termination of the filling process, the syringe 14 may be disengaged from the port 430 and the inlet block 200 may be moved back to the decapping position. In turn, the syringe may be engaged with the cap 30 that is retained within the decapping cavity 510. Once reengaged, the shuttle 212 may be moved beyond the decapping position such that the first portion 512 and the second portion 514 of the cap retention cavity 510 are disposed in the open position and the syringe 14 may be withdrawn with the cap 30 disposed on the syringe 14. With further reference to FIG. 22, the cap retention cavity 510 may have a biased button 520 that may act upon a cap 30 retained within the cap retention cavity 510 to eject the cap 30 from the cap retention cavity 510 upon movement of the first and second portion 512 and 514 of the cap retention cavity 510 to the open position.

Specifically, with further reference to FIG. 17, the button 520 may comprise a surface 530 that is contacted by the cap 30 when the cap 30 is advanced into the cap retention cavity 510 as the syringe 14 is advanced toward the cap retention cavity 510 along the predetermined axis A-A. In turn, the button 520 may be secured to the slide 502 by a fastener 526. The fastener 526 may engage a threaded portion 524 of the button 520. The fastener 526 may be engaged with the button 520 to allow for movement of the button relative to the slide 502 (e.g., in a direction along axis A-A when the decapping mechanism 500 is in the decapping position). In turn, a biasing member 522 may be provided that may bias the button 520 away from the slide 502. In turn, as a cap 30 is introduced into the cap retention cavity 510, the button 520 may be contacted and moved against a biasing force of the biasing member 522. In turn, when a cap 30 is released, the cap 30 may be urged out of the cap retention cavity 510.

This may be useful to dampening and tolerance absorption. Furthermore, it may assist in ejecting a cap 30 from the cap retention cavity 510. For instance, in certain instances, it may be advantageous to manually clear a cap 30 from the cap retention cavity 510. With returned reference to FIGS. 2 and 3, the slide 502 may include an extension 532. In turn, in the event that a cap 30 is to be manually ejected, the inlet block 200 may move to a position such that the extension 532 is accessible by a user. The user may then manually move the slide 502 relative to the shuttle 212 (e.g., overcoming the biasing force of the spring-loaded shoulder bolt 504 to open the cap retention cavity 510). In turn, the cap 30 may be ejected from the cap retention cavity 510 by the button 520.

In addition to the decapping mechanism 500, which is generally provided on the inlet block 200 described above, an additional or alternative cap gripping device 700 may also be provided. For instance, as shown in FIG. 3, the cap gripping device 700 may be arranged separately from the inlet block 200. However, as will be described in greater detail below, the inlet block 200 (e.g., movement of the inlet block 200 into a given position) may be utilized to actuate the cap gripping device 700. In this regard, the cap gripping device 700 may be utilized to engage and retain a cap 30 of a syringe 14 and may be utilized, for example, in conjunction with or independent from the decapping mechanism 500 to engage and retain a cap 30 during a different operation of the automated filling device 10.

Figure 29:
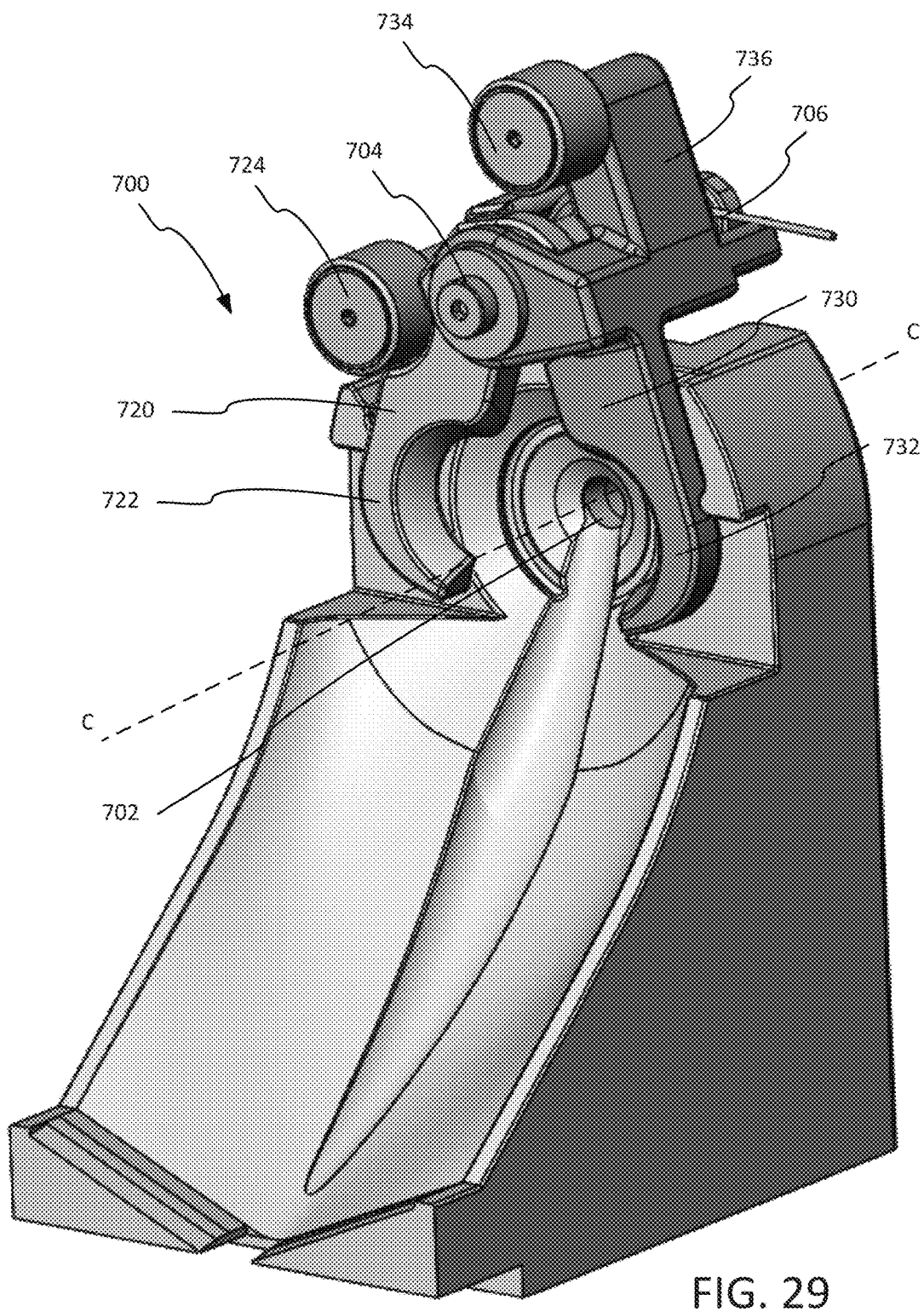
FIG. 29 depicts a perspective view of an embodiment of a cap gripping device.

For instance, as shown in FIG. 3, the cap gripping device 700 may be disposed relative to a portion of a syringe positioning member 710. In this regard, the cap gripping device 700 may include an aperture 702 for receiving a cap 30 of a syringe 14 that may be aligned on a predetermined axis C-C as depicted in FIG. 29. With reference to FIG. 3, axis C-C may be parallel to axis A-A and offset therefrom. Specifically, axis A-A and axis C-C may line in a common plane. In turn, a syringe gripping apparatus that may be operative to engage and move a syringe may be provided (although not shown). In any regard, given that predetermined axis C-C and predetermined axis A-A may lie in a common plane, a syringe gripping apparatus may be operative to move the syringe 14 in two dimensions corresponding to the two dimensions in which the plane (defined by axis A-A and axis C-C) extends. The axis B-B, corresponding to the first dimension in which the inlet block 200 is moveable, may be disposed at an angle relative to the plane in which axes A-A and C-C extend. In turn and as will be discussed in greater detail below, movement of the inlet block 200 in the first dimension along axis B-B may allow for positioning of the decapping mechanism 500 on the predetermined axis A-A and may allow for actuation of the cap gripping device 700. This arrangement may provide simplicity as the syringe gripping apparatus may move in only two dimensions corresponding to the plane in which axes A-A and C-C extend and the inlet block 200 may move only in the first dimension corresponding to axis B-B.

With further reference to FIG. 29, the cap gripping device 700 may include a first jaw member 720 and a second jaw member 730. The first jaw member 720 may comprise a cap engagement portion 722 that is configured to engage a contour of a cap 30 (e.g., similar to the barbs 528 described and shown above in relation to FIG. 17). The second jaw member 730 may also comprise a cap engagement portion 732.

The first jaw member 720 and the second jaw member 730 may be engaged for relative motion between an open position and a closed position. Specifically, the first jaw member 720 and the second jaw member 730 may be disposed for pivotal motion about an axle 704. The first jaw member 720 and the second jaw member 730 may be biased into the open position as shown in FIG. 29. For instance, one or more biasing members 706 may be provided to bias the first jaw member 720 and the second jaw member 730 in the open position. A single biasing member 706 may be provided that acts on both jaw members 720 and 730 to bias the jaw members into the open position. Alternatively, corresponding respective biasing members 706 may be provided to act on the first jaw member 720 or the second jaw member 730, respectively.

In any regard, the first jaw member 720 may include a first cam follower 724. The second jaw member 730 may include a second cam follower 734 that may be engaged by a cam. The cam followers 724 and 734 may comprise corresponding respective rollers that may be engaged by a cam. The first cam follower 724 may be disposed between the axle 704 and the cap engagement portion 722 of the first jaw member 720. In contrast, the second cam follower 734 may be disposed on a lever arm 736 that disposes the second cam follower 734 on a side of the axle 704 opposite the cap engagement portion 732 of the second jaw member 730. Accordingly, engagement of the respective first and second cam followers 724 and 734 by a cam acting in a common direction relative to the first cam follower 724 and the second cam follower 734 may result in opposite movement of the respective jaw members 720 and 730 about the axle 704.

That is, when the first cam follower 724 is engaged by a cam to move the first cam follower 724 in the common direction, the first jaw member 722 may undergo movement in a first direction (e.g., anticlockwise) about the pivot 704. When the second cam follower 734 is engaged by a cam to move the second cam follower 734 in the common direction, the second jaw member 730 may undergo movement in a second direction opposite the first direction (e.g., clockwise) about the pivot 704. In turn, the first cam follower 724 and the second cam follower 726 may be engaged by a common cam to move the followers 724 and 734 in a common direction. However, opposite motion of the jaw members 720 and 730 may be imparted to move the jaw members 720 and 730 to a closed position. In an embodiment, the inlet block 200 may comprise the cam utilized to engage the followers 724 and 734 to move the jaw members 720 and 730 from the open position to the closed position against the force of the biasing member(s) 706.

Figure 30:
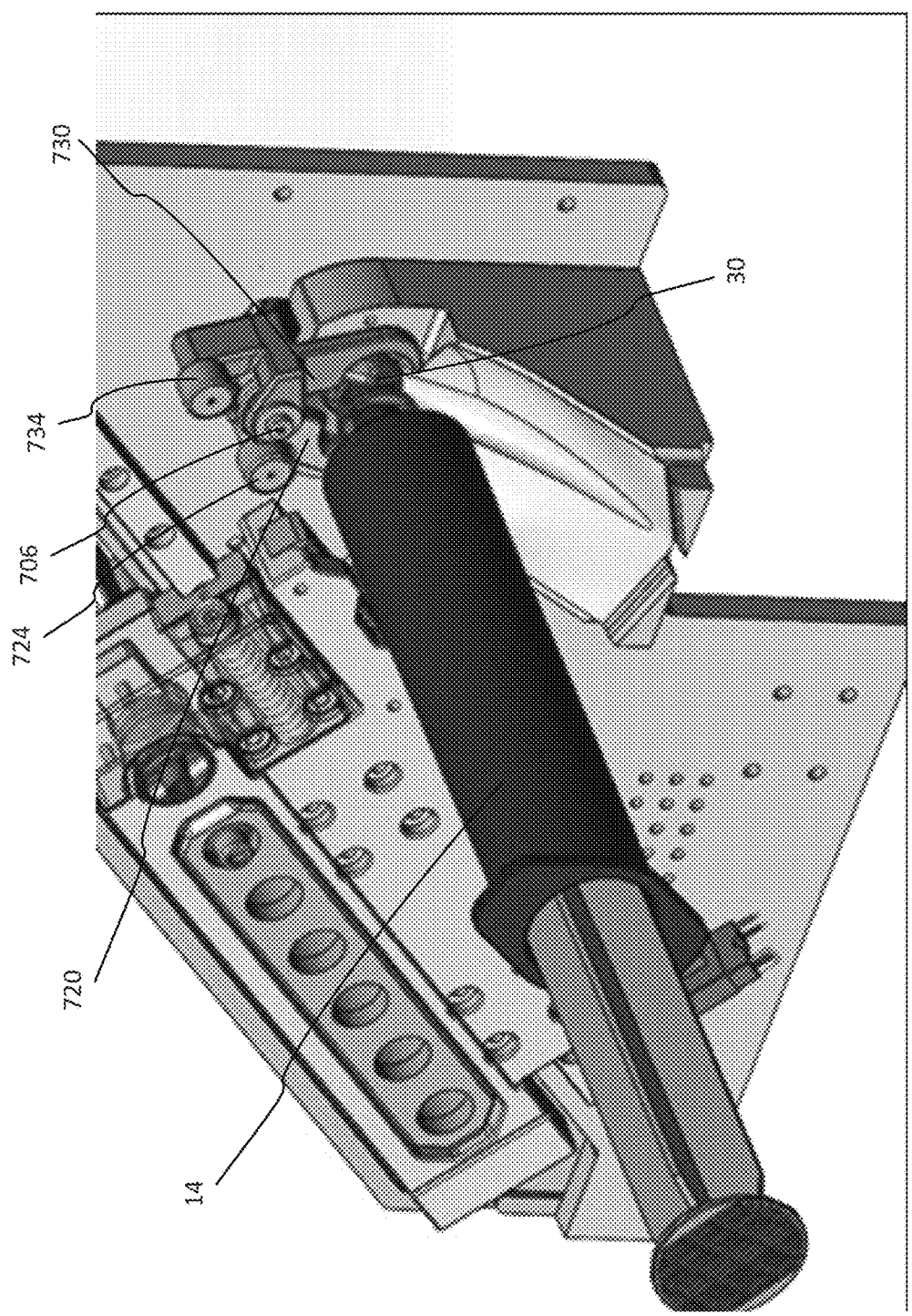
FIG. 30 depicts a perspective view of an embodiment of a cap gripping device with a cap of a syringe disposed relative to the cap gripping device in an open position.
Figure 31:
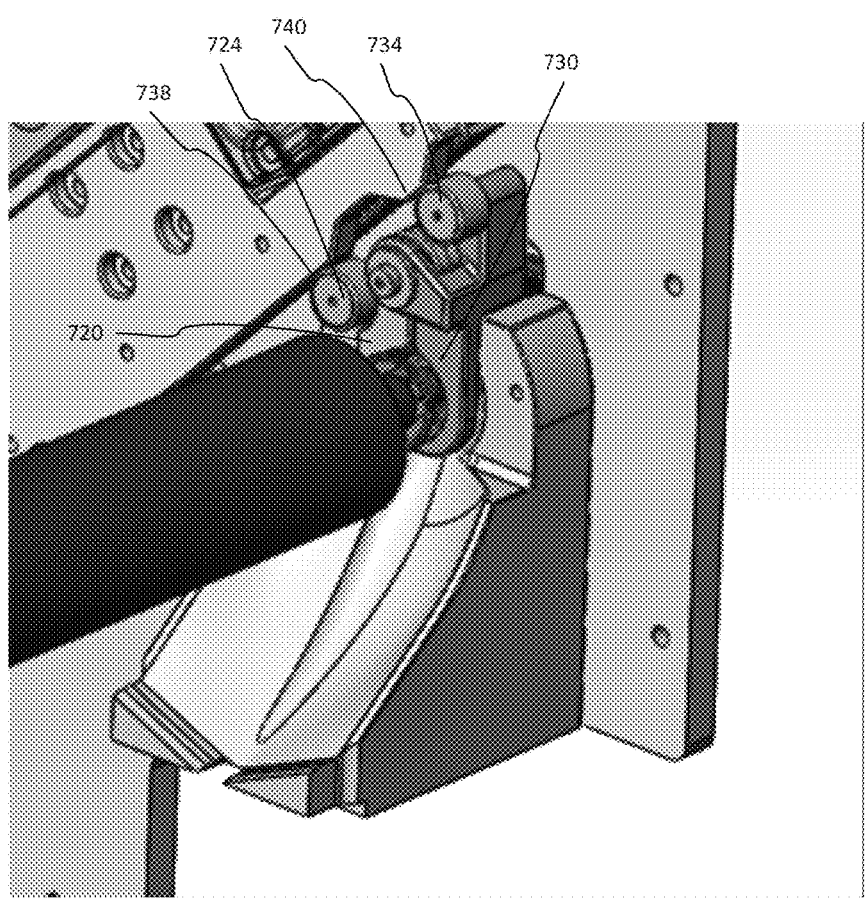
FIG. 31 depicts a perspective view of an embodiment of a cap gripping device with a cap of a syringe disposed relative to the cap gripping device in a closed position as actuated by an inlet block of a source fluid inlet assembly.
Figure 32:
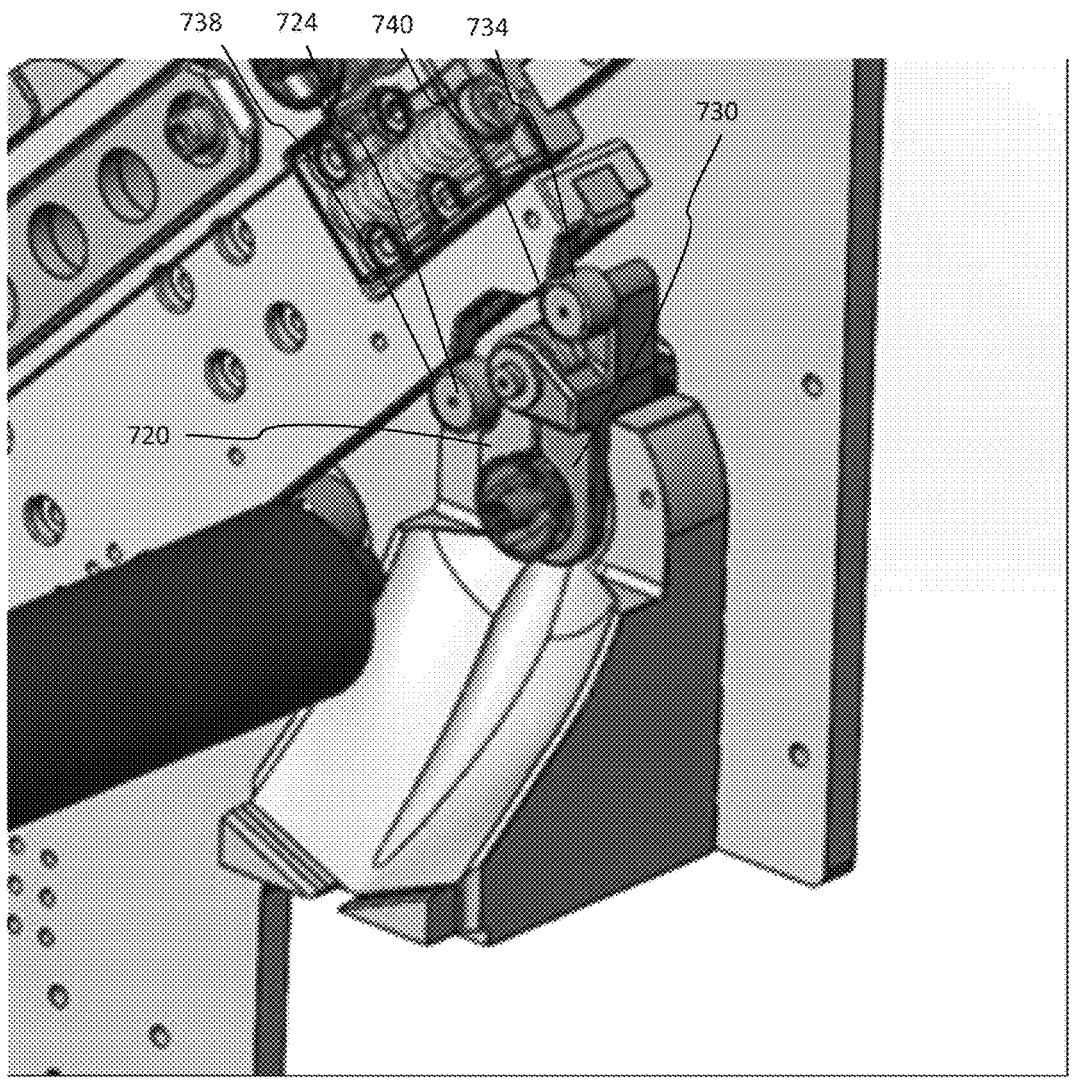
FIG. 32 depicts a perspective view of an embodiment of a cap gripping device with a cap of a syringe disposed relative to the cap gripping device in a closed position as actuated by an inlet block of a source fluid inlet assembly with a syringe withdrawn therefrom to decap the syringe.

For instance, with further reference to FIG. 30, a syringe 14 may be disposed to position a cap 30 disposed on the syringe 14 relative to the aperture 702 as shown in FIG. 30. In this position, the first jaw member 720 and the second jaw member 730 may be biased into the open position to allow for positioning of the cap 30 relative to the aperture 702. With further reference to FIG. 31, the inlet block 200 may be moved to an actuation position. In this regard, a first cam surface 738 and a second cam surface 740 defined on the inlet block 200 may contact the first cam follower 724 and the second cam follower 726. In turn, the first cam follower 724 may be displaced in the common direction away from the inlet block 200 to impart motion of the first jaw member 720 in the first direction. Additionally, the second cam follower 734 may be displaced in the common direction away from the inlet block 200 to impart motion of the second jaw member 730 in the second direction. In turn, the first jaw member 720 and the second jaw member 730 may be moved to the closed position to engage the cap 30 disposed relative to the aperture 702 as shown in FIG. 32. With further reference to FIG. 32, while the first jaw member 720 and second jaw member 730 engage the cap 30, the syringe 14 may be moved away from the cap 30 in a direction along axis C-C. In turn, the cap 30 may be removed to allow manipulation of the syringe 14 (e.g., to expose the syringe for filling and/or purging operations).

Figure 33:
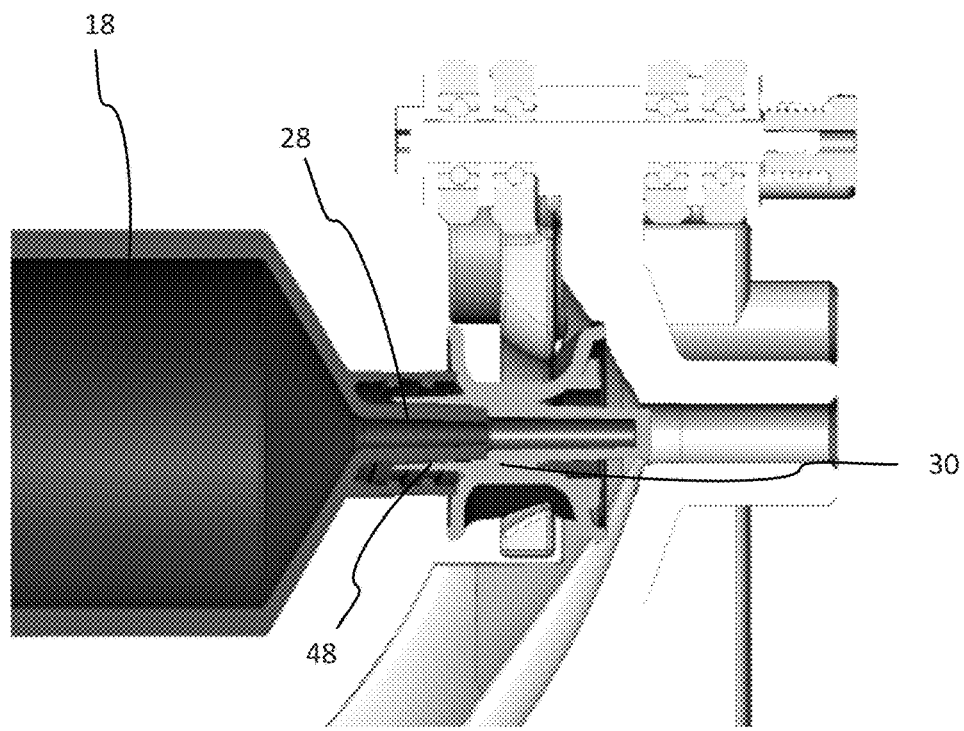
FIG. 33 depicts an embodiment of a cap gripping device in cross section with a cap of a syringe engaged with the cap gripping device.
Figure 34:
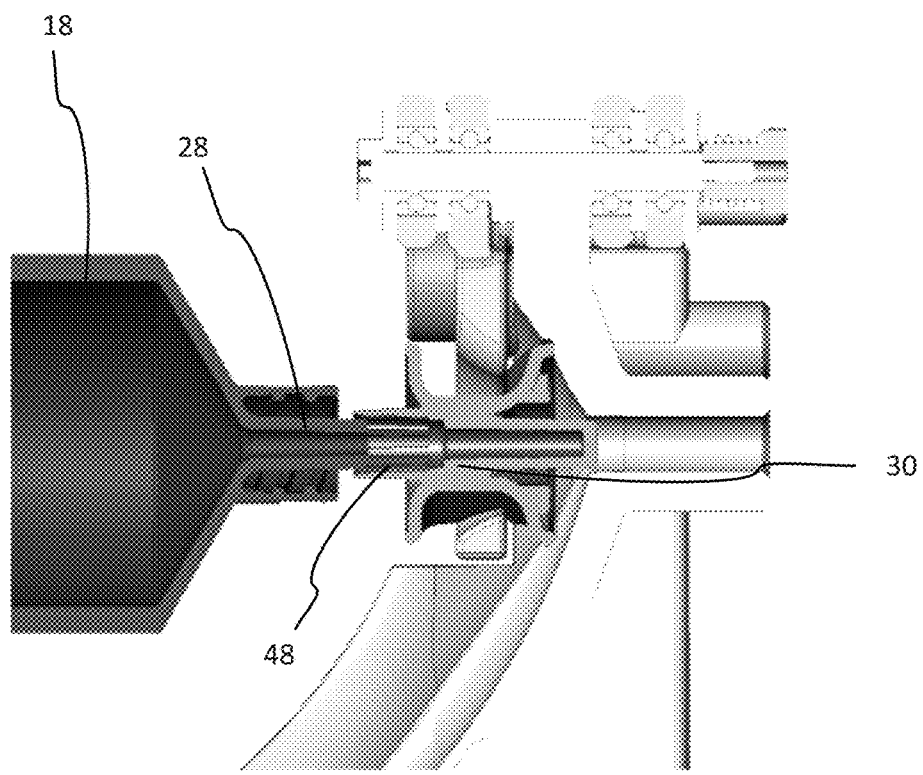
FIG. 34 depicts an embodiment of a cap gripping device in cross section with a cap of a syringe engaged with the cap gripping device and a syringe withdrawn from the cap for a purging operation.

In relation to purging operations, syringes 14 may be provided with the plunger of the syringe 14 slightly retracted. In this regard, the syringe 14 may be purged or "burped" prior to undergoing filling. Whether performed at the cap gripping device 700 or the decapping mechanism 500, the syringe 14 may be retracted slightly from the cap 30 such that a tortious path is maintained in relation to sterile surfaces of the syringe tip 28. For instance, with further reference to FIG. 33, the syringe tip 18 may, initially, be fully seated in an opening 48 of the cap 30. In turn, upon engagement of the cap 30 and retraction of the syringe 14, the syringe 14 may be retracted such that the distal end of the syringe tip 18 remains within the opening 48, yet spaced apart from the opening 48 to allow for a fluid path to facilitate purging of the syringe 14. As such, when disposed in the position shown in FIG. 34 with the syringe tip 18 still within but spaced apart from the opening 48, the plunger 18 may be advanced relative to the barrel 14 to purge the syringe 14 of air. The purging may be accomplished by a device within the automated filling device 10 that may manipulate the plunger 18. For instance, a second positioning member may be advanced relative to the syringe 14 when the syringe is maintained in the purging position shown in FIG. 34 to advance the plunger 18 to purge the syringe 14.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A source fluid inlet for an automated filling device, comprising:
   an inlet block comprising a port configured to accept a source fluid tube set;
   a track with which the inlet block is engaged, the track defined by at least one rail, wherein the inlet block and the track are disposed for relative movement between the inlet block and the track for positioning of the inlet block in a plurality of positions in a first dimension relative to the track at least including:

a load position, wherein the port is aligned with a recess in the at least one rail to facilitate engagement of a source fluid tubing set with the port, and a fill position, wherein the port is disposed relative to a predetermined axis along which a syringe is moveable for selective engagement of a syringe with a source fluid tubing set engaged with the port to establish fluid communication between a syringe and a source fluid tubing set engaged with the port.

2. The source fluid inlet of claim 1, further comprising:
a reader disposed relative to the inlet block to read a machine readable indicia provided on a source fluid tube set disposed in the port.

3. The source fluid inlet of claim 1, wherein when away from the load position, the at least one rail extends relative to the port to prevent removal or insertion of a source fluid tubing set from the port.

4. The source fluid inlet of claim 3, wherein the port further comprises a groove that is configured to receive a flange of a connector of a source fluid tubing set; wherein the groove comprises a terminal portion disposed proximally relative to a distal opening of the port such that a sheath having at least one finger disposed distal relative to a fill connection of the connector engages the terminal portion of the groove prior to the connector being fully advanced relative to the port.

5. The source fluid inlet of claim 4, wherein the terminal portion of the groove limits distal movement of a sheath of a connector engaged with the port such that a first portion of a connector comprising a fill connection is advanceable distally relative to a sheath in response to further distal advancement of a connector relative to the port when a flange of a connector engages the terminal portion of the groove.

6. The source fluid inlet of claim 1, wherein the inlet block comprises:
a shuttle disposed adjacent to the track for movement relative to the track; and
a cartridge defining the port and comprising a first portion selectively engageable with the shuttle for co-movement with the shuttle and a second portion extending relative to the track for engagement with the track.

7. The source fluid inlet of claim 6, wherein the second portion comprises a channel in which the at least one rail is disposed when the inlet block is away from the load position; and
wherein a neck of a source fluid tube set is alignable with the channel when engaged with the port, and wherein a shoulder of a source fluid tube set is moveable at least a first distance beyond the channel in the port when a source fluid tube set is engaged with the port.

8. The source fluid inlet of claim 6, wherein the cartridge is replaceable.

9. The source fluid inlet of claim 8, wherein the track comprises a moveable portion that is operative to displace at least a portion of the rail to facilitate engagement of the cartridge with the shuttle.

10. The source fluid inlet of claim 9, wherein the moveable portion comprises an interlock to detect when the moveable portion is in an open position relative to the track.

11. The source fluid inlet of claim 1, wherein the inlet block comprises:
a shuttle disposed adjacent to the track for movement relative to the track, wherein the shuttle comprises a first portion of a cap retention cavity; and a slide member comprising a second portion of the cap retention cavity, wherein the first portion of the cap retention cavity and the second portion of the cap retention cavity are disposed for relative movement between an open position and a closed position.

12. The source fluid inlet of claim 11, wherein the slide member is supportably engaged by the shuttle and biased into the closed position by a biasing member, the slide member further comprising:
a tab engageable with a stop to restrict continued movement beyond a predetermined point in the first dimension, and wherein the shuttle is moveable beyond the predetermined point to apply a force against a biasing force of the biasing member move the first portion of the cap retention cavity and the second portion of the cap retention cavity into the open position.

13. The source fluid inlet of claim 12, wherein the inlet block is positionable in the first dimension relative to the track in a decapping position in which the cap retention cavity is aligned with the predetermined axis, and wherein a syringe having a cap disposed thereon is moveable along the predetermined axis to dispose the cap in the cap retention cavity when in the open position such that the cap is retained in the cap retention cavity upon movement of the first portion of the cap retention cavity and the second portion of the cap retention cavity to the closed position.

14. The source fluid inlet of claim 11, further comprising:
a cap gripping device comprising a first jaw member and a second jaw member, wherein the first jaw member and the second jaw member are disposable in an open position and a closed position, wherein the cap gripping device is disposed in relation to a second predetermined axis offset and parallel to the predetermined axis.

15. The source fluid inlet of claim 14, wherein the first jaw member comprises a first cam follower and the second jaw member comprises a second cam follower, and wherein the first cam follower and the second cam follower are engageable by corresponding respective cam surfaces on the inlet block when the inlet block is in an actuation position in the first dimension to move the first and second cam followers in a common direction to dispose the first jaw member and the second jaw member in the closed position.

16. The source fluid inlet of claim 15, wherein the predetermined axis and the second predetermined axis define a plane extending in two dimensions, wherein a syringe positioning apparatus is operative to move a syringe in the two dimensions, and wherein the first dimension extends at an angle relative to the plane.

17. The source fluid inlet of claim 1, further comprising:
a single plate capacitive sensor disposed along the track such that the single plate captive sensor is operative to monitor a source fluid tubing set engaged with the port when in the fill position.

18. The source fluid inlet of claim 17, wherein the single plate capacitive sensor is disposed relative to the track such that the sensor is disposed on only a first side of a source fluid tubing set engaged with the port.

19. The source fluid inlet of claim 18, wherein the single plate capacitive sensor is disposed in the at least one rail that is disposable relative to a neck of a source fluid tube set engaged with the port.

* * * * *